(12) United States Patent
Soucy et al.

(10) Patent No.: US 6,794,516 B2
(45) Date of Patent: Sep. 21, 2004

(54) SYNTHESIS OF CLASTO-LACTACYSTIN β-LACTONE AND ANALOGS THEREOF

(75) Inventors: François Soucy, Arlington, MA (US); Louis Plamondon, Watertown, MA (US); Mark Behnke, Somerville, MA (US); William Roush, Ann Arbor, MI (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 162 days.

(21) Appl. No.: 10/360,459

(22) Filed: Feb. 7, 2003

(65) Prior Publication Data

US 2003/0191322 A1 Oct. 9, 2003

Related U.S. Application Data

(62) Division of application No. 09/927,980, filed on Aug. 10, 2001, now Pat. No. 6,566,553, which is a division of application No. 09/597,514, filed on Jun. 20, 2000, now Pat. No. 6,294,560, which is a division of application No. 09/134,674, filed on Aug. 14, 1998, now Pat. No. 6,133,308.
(60) Provisional application No. 60/067,352, filed on Dec. 3, 1997, and provisional application No. 60/055,848, filed on Aug. 15, 1997.

(51) Int. Cl.$^7$ ............................................. C07D 263/08
(52) U.S. Cl. ........................................................ 548/239
(58) Field of Search ........................................... 548/239

(56) References Cited

U.S. PATENT DOCUMENTS

| | | | | |
|---|---|---|---|---|
| 5,831,068 A | * | 11/1998 | Nair et al. ................. | 536/24.5 |
| 5,942,494 A | | 8/1999 | Ginsberg et al. ............... | 514/18 |
| 6,271,199 B2 | | 8/2001 | Brand et al. .................... | 514/2 |

FOREIGN PATENT DOCUMENTS

WO    WO 96/32105    * 10/1996

OTHER PUBLICATIONS

S. Choi, "Total Syntheses of (6R)–Lactacystin and Beta––Lactone Derivatives,"; Chpt. 3, Dissertation, Dept. of Chemistry, Harvard University, 1995.*
Chida, N. et al., J. Chem. Soc., Chem. Comm. 7(7):793–4, 1995.*
Corey et al., J. Am. Chem. Soc., 114(26): 10677–78, 1992.*
Corey et al., Tetrahedron Letters 34(44): 6969–72, 1993.*
Corey et al., Tetrahedron Letters 34(44) 6973–76, 1993.*
Corey et al., Tetrahedron Letters 34(44): 6977–80, 1993.*
Dikshit et al., Tetrahedron Letters 36(34): 6131–34, 1995.*
Fenteany et al., Proc. Natl. Acad. Sci. USA 91:3358–62, 1994.*
Fenteany et al., Science 268:726–31, 1995.*
Nagamitsu et al., J. Am. Chem. Soc. 118:3584–90, 1996.*
Nakagawa et al., Tetrahedron Letters 35(28):5009–12, 1994.*
Sunazuka et al., J. Am. Chem. Soc. 115:5302, 1993.*
Uno et al., J. Am. Chem. Soc. 116:2139–40, 1994.*
WPI Derwent Accession No. 96–485455, English Abstract of WO 96/32105, 1996.*
Shibata et al., Tetrahedron Letters 37:2791–94, 1996.*
Wipf et al., Tetrahedron Letters 37:4659–62, 1996.*
Omura, et al., "Structure of Lactacystin, A New Microbial Metabolite Which Induces Differentiation of Neuroblastoma Cells" *J. Antibiotics* 1991, 44(*1*): 117–118.
Omura, et al., "Lactacystin, A Novel Microbial Metabolite, Induces Neuritogenesis of Neuroblastoma Cells" *J. Antibiotics* 1991, 44(*1*): 113–116.
Dick et al., "Mechanistic Studies on the Inactivation of the Proteasome by Lactacystin" *J. Biol. Chem.* 1996 271(*13*): 7273–7276.
Haddad et al., "Asymmetric Synthesis of the Abbott Amino Dihydroxyethylene Dipeptide Isostere Subunit" *Tetrahedron Lett.* 1996, 37(*26*): 4525–4528.
Wang, et al., "Large–Scale and Highly Enantioselective Synthesis of the Taxol C–13 Side Chain through Asymmetric Dihydroxylation" *J. Org. Chem.* 1994, 59:5104–5105.

* cited by examiner

*Primary Examiner*—Joseph K. McKane
*Assistant Examiner*—Kamal Saeed
(74) *Attorney, Agent, or Firm*—Hale and Dorr LLP

(57) ABSTRACT

The present invention is directed to an improved synthesis of clasto-lactacystin-β-lactone, and analogs thereof, that proceeds in fewer steps and in much greater overall yield than syntheses described in the prior art. The synthetic pathway relies upon a novel stereospecific synthesis of an oxazoline intermediate and a unique stereoselective addition of a formyl amide to the oxazoline. Also described are novel clasto-lactacystin-β-lactones, and analogs thereof and their use as proteosome inhibitors.

23 Claims, 2 Drawing Sheets

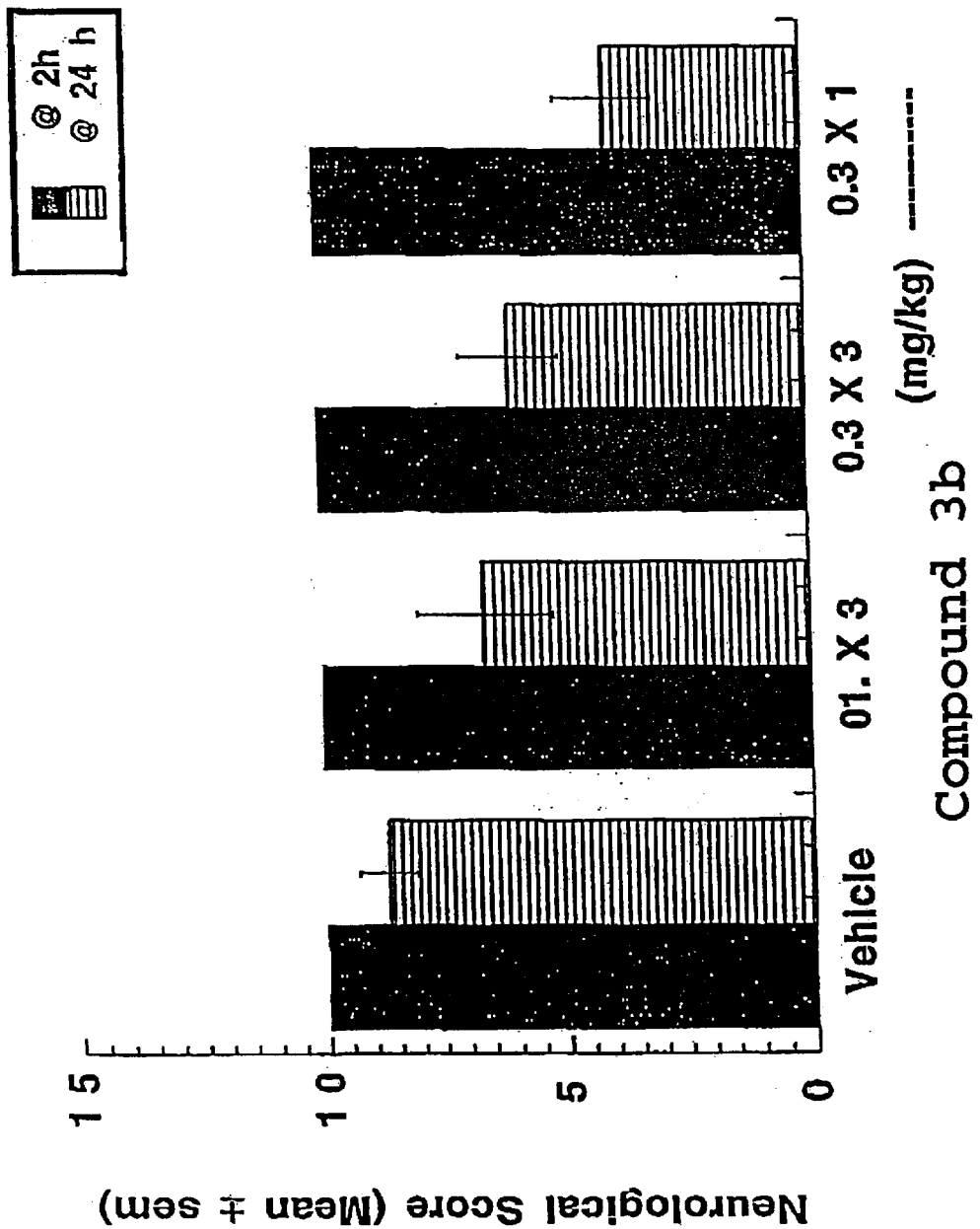

SYNTHESIS OF CLASTO-LACTACYSTIN β-LACTONE AND ANALOGS THEREOF

CROSS REFERENCE TO RELATED APPLICATIONS

This application is a divisional of U.S. patent application Ser. No. 09/927,980, filed on Aug. 10, 2001 now U.S. Pat. No. 6,566,553, which is a divisional U.S. patent application Ser. No. 09/597,514, filed on Jun. 20, 2000 now U.S. Pat. No. 6,294,560, which is a divisional of U.S. patent application Ser. No. 09/134,674, filed on Aug. 14, 1998, now U.S. Pat. No. 6,133,308, which in turn claims priority form U.S. Provisional Patent Application Serial No. 60/055,848, filed on Aug. 15, 1997, and U.S. Provisional Patent Application Serial No. 60/067,352, filed on Dec. 3, 1997, all of which applications are hereby incorporated by reference.

BACKGROUND OF THE INVENTION

1. Field of the Invention

The invention relates generally to methods for preparing lactacystin and related compounds, to novel analogs of lactacystin and clasto-lactacystin β-lactone, and their uses as proteasome inhibitors.

2. Description of Related Art

The Streptomyces metabolite lactacystin (1) inhibits cell cycle progression and induces neurite outgrowth in cultured neuroblastoma cells (Omura et al., *J. Antibiotics* 44:117 (1991); Omura et al., *J. Antibiotics* 44:113 (1991); Fenteany et al., *Proc. Natl. Acad. Sci.* (*USA*) 91:3358 (1994)). The cellular target mediating these effects is the 20S proteasome, the proteolytic core of the 26S proteasome, which is the central component of the ubiquitin-proteasome pathway for intracellular protein degradation. Mechanistic studies have established that lactacystin inhibits the proteasome through the intermediacy of the active species, clasto-lactacystin β-lactone (2), which specifically acylates the N-terminal threonine residue of the proteasome X/MB1 subunit (Fenteany, et al., *Science* 268:726 (1995); Dick et al., *J. Biol. Chem.* 271:7273 (1996)). Lactacystin analogs are disclosed by Fenteany et al. (WO 96/32105).

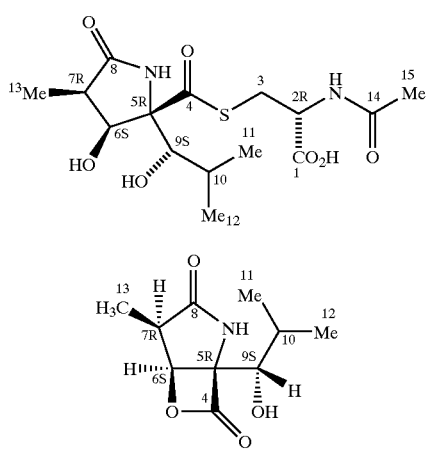

The ubiquitin-proteasome pathway is involved in a variety of important physiological processes (Goldberg et al., *Chemistry & Biology* 2:503 (1995); Ciechanover *Cell* 79:13 (1994); Deshaies, *Trends Cell Biol.*5:431 (1995)). In fact, the bulk of cellular proteins are hydrolyzed by this pathway. Protein substrates are first marked for degradation by covalent conjugation to multiple molecules of a small protein, ubiquitin. The resultant polyubiquitinated protein is then recognized and degraded by the 26S proteasome. Long recognized for its role in degradation of damaged or mutated intracellular proteins, this pathway is now also known to be responsible for selective degradation of various regulatory proteins. For example, orderly cell cycle progression requires the programmed ubiquitination and degradation of cyclins. The ubiquitin-proteasome pathway also mediates degradation of a number of other cell cycle regulatory proteins and tumor suppressor proteins (e.g., p21, p27, p53). Activation of the transcription factor NF-κB, which plays a central role in the regulation of genes involved in the immune and inflammatory responses, is dependent upon ubiquitination and degradation of an inhibitory protein, IκB-α (Palombella et al., WO 95/25533). In addition, the continual turnover of cellular proteins by the ubiquitin-proteasome pathway is essential to the processing of antigenic peptides for presentation on MHC class I molecules (Goldberg and Rock, WO 94/17816).

The interesting biological activities of lactacystin and clasto-lactacystin β-lactone and the scarcity of the natural materials, as well as the challenging chemical structures of the molecules, have stimulated synthetic efforts directed toward lactacystin and related analogs. Corey and Reichard *J. Am. Chem. Soc.* 114:10677 (1992); *Tetrahedron Lett.* 34:6977 (1993)) achieved the first total synthesis of lactacystin, which proceeded in 15 steps and 10% overall yield. The key feature of the synthesis is a stereoselective aldol reaction of a cis-oxazolidine aldehyde derived from N-benzylserine to construct the C(6)–C(7) bond. In the synthesis reported by (Uno et al., *J. Am. Chem. Soc.* 116:2139 (1994)), stereoselective Mukaiyama-aldol reaction of a bicyclic oxazolidine silyl enol ether intermediate derived from, D-pyroglutamic acid is employed in C(5)–C (9) bond construction. This synthesis proceeds in 19 steps and 5% overall yield. Aldol reactions under basic conditions of a similar bicyclic oxazolidine intermediate form the basis of model studies reported by (Dikshit et al., *Tetrahedron Lett.* 36:6131 (1995)).

Aldol reactions of oxazoline-derived enolates feature prominently in the synthesis of lactacystin reported by Smith and coworkers (Suazuka et al, *J. Am. Chem. Soc.* 115:5302 (1993); Nagamitsu et al., *J. Am. Chem. Soc.* 118:3584 (1996)) and in the synthesis of (6R)-lactacystin reported by (Corey and Choi *Tetrahedron Lett.* 34:6969 (1993)); Choi Ph.D., Thesis, Harvard University, 44 (1995). In the former synthesis, which proceeds in 20 steps and 9% overall yield, the enolate is condensed with formaldehyde to install a single carbon atom, which must then be elaborated in a number of additional steps. In the Corey and Choi synthesis, the aldol reaction selectively provides the product of undesired stereochemistry, resulting in the eventual preparation of the C(6) epimer of lactacystin, which is devoid of biological activity.

Lactacystin has also been prepared in 22 steps and 2% overall yield from D-glucose (Chida et al., *J. Chem. Soc., Chem. Commun.* 793 (1995)). The biosynthetic pathway involved in production of the natural product has been investigated in feeding experiments involving $^{13}$C-enriched compounds (Nakagawa et al., *Tetrahedron Lett.* 35:5009 (1994)).

The reported syntheses of lactacystin are lengthy and proceed in low yield. Furthermore, none of these syntheses is readily adapted for analog synthesis. Thus, there is a need for improved methods for preparing lactacystin, clasto-lactacystin β-lactone, and analogs thereof.

SUMMARY OF THE INVENTION

A first aspect of the present invention relates to a process for forming lactacystin or analogs thereof having Formula VI or clasto-lactacystin β-lactone or analogs thereof having Formula VII:

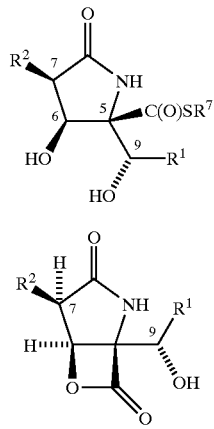

wherein $R^1$ is alkyl, alkenyl, alkynyl, cycloalkyl, aryl, alkaryl, aralkyl, where the ring portion of any of said aryl, aralkyl, or alkaryl can be optionally substituted;

$R^2$ is alkyl, cycloalkyl, aryl, alkaryl, aralkyl, alkoxy, hydroxy, alkoxyalkyl, or amido, where the ring portion of any of said aryl, aralkyl, or alkaryl can be optionally substituted; and $R^7$ is alkyl, aryl, aralkyl, alkaryl, wherein any of said alkyl, aryl, aralkyl or alkaryl can be optionally substituted.

A second aspect of the present invention is directed to a method of forming formyl amides of Formula XIV:

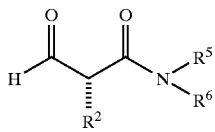

where $R^2$ is alkyl, cycloalkyl, aryl, alkaryl, aralkyl, alkoxy, hydroxy, alkoxyalkyl, or amido, where the ring portion of any of said aryl, aralkyl, or alkaryl can be optionally substituted; and $R^5$ and $R^6$ are independently one of alkyl or alkaryl; or $R^5$ and $R^6$ when taken together with the nitrogen atom to which they are attached form a 5- to 7-membered heterocyclic ring, which may be optionally substituted, and which optionally may include an additional oxygen or nitrogen atom.

A third aspect of the present invention relates to forming tri-substituted oxazolines of Formula Ia or Ib:

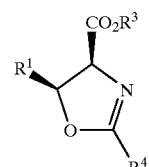

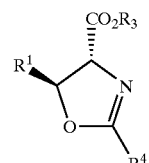

where $R^1$ is alkyl, alkenyl, alkynyl, cycloalkyl, aryl, alkaryl, aralkyl, where the ring portion of any of said aryl, aralkyl, or alkaryl can be optionally substituted; and $R^4$ is aryl or heteroaryl, either of which may be optionally substituted. The tri-substituted oxazolines of Formulae Ia and Ib are useful as starting materials in forming lactacysin, clasto-lactacystin β-lactone or analogs thereof via the process described herein.

A fourth aspect of the present invention is directed to lactacysin, clasto-lactacystin β-lactone or analogs of Formulae VI and VII that possess unexpected biological activity. Lactacystin, clasto-lactacystin β-lactone, and analogs thereof possess biological activity as inhibitors of the proteasome. They can be used to treat conditions mediated directly by the function of the proteasome, such as muscle wasting, or mediated indirectly via proteins which are processed by the proteasome, such as the transcription factor NF-κB.

A fifth aspect of the present invention relates to pharmaceutical compositions, comprising a compound of Formula VI or Formula VII, and a pharmaceutically acceptable carrier or diluent.

A sixth aspect of the present invention relates to methods of inhibiting proteasome function or treating a condition that is mediated directly or indirectly by the function of the proteasome, by administering a compound of Formula VI or Formula VII that possesses unexpectedly high activity in inhibiting the proteasome. Preferred Embodiments are directed to the use of a compound of Formulae VI or VII to prevent or reduce the size of infarct after vascular occlusion for example, for treating neuronal loss following stroke. An additional preferred embodiment is directed to the use of said compounds for treating asthma.

A seventh aspect of the invention relates to enantiomerically-enriched compositions of formyl amides of Formula XIV.

An eighth aspect of the present invention relates to novel individual intermediates, such as aldols of Formula II and aminodiols of Formula III:

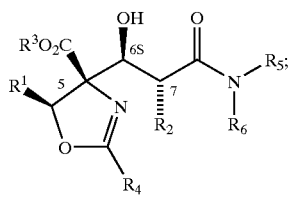

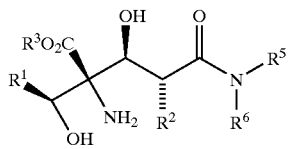

III and individual steps within the multistep process for forming lactacystin, clasto-lactacystin β-lactone or various analogs thereof.

A ninth aspect of the present invention relates to individual intermediates, such as compounds of Formulae XVII, XVIII and XIX:

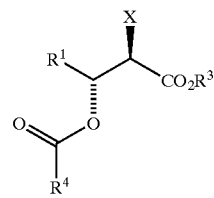

XVIIa

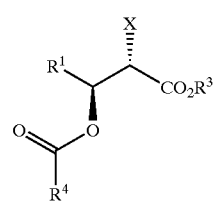

XVIIb

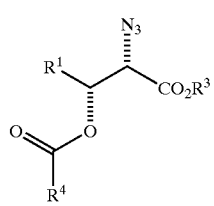

XVIIIa

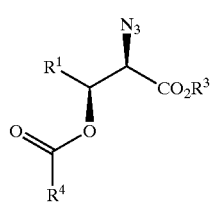

XVIIIb

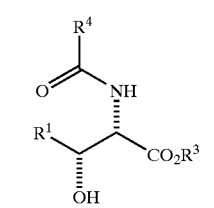

XIXa

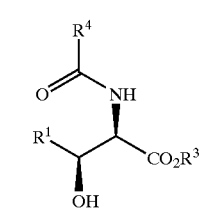

XIXb where X is a halogen, preferably Cl, Br or I, as well as individual steps within the multistep process for forming substituted oxazolines of Formula I.

Other features or advantages of the present invention will be apparent from the following detailed description, and also from the appending claims.

BRIEF DESCRIPTION OF THE DRAWINGS

FIG. 2. depicts a graph showing the effect of compound 3b, administered i.v. on neurological score in rats (n=6–8).

DETAILED DESCRIPTION OF THE PREFERRED EMBODIMENTS

Figure 1:
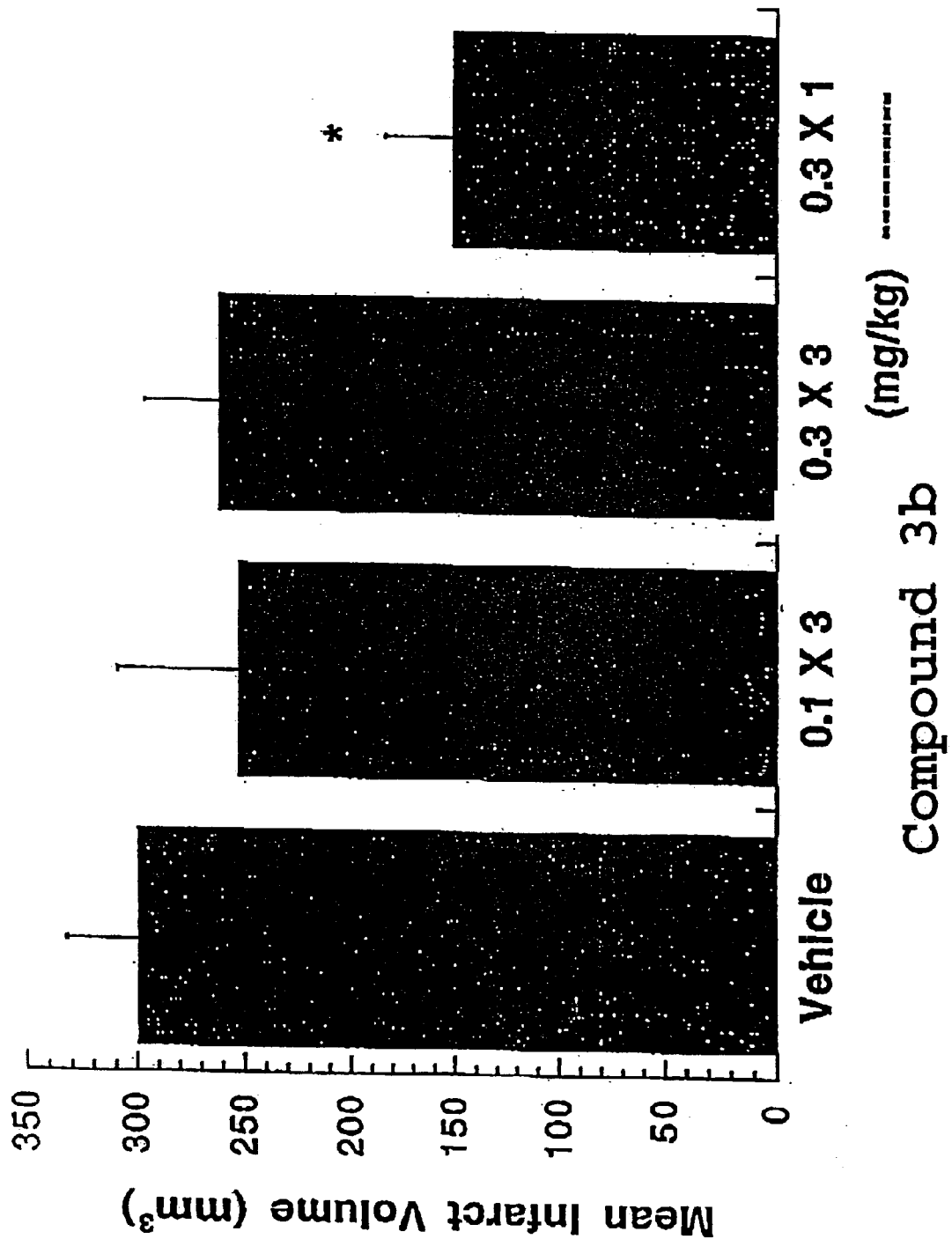
FIG. 1. depicts a graph showing the effect of compound 3b, administered i.v., on infarct volume in rats (n=6–8).

The present invention relates to an improved multi-step synthesis of lactacystin, clasto-lactacystin β-lactone, and analogs thereof, that proceeds in fewer steps and in much greater overall yield than syntheses described in the prior art. A number of individual process steps and chemical intermediates distinguish this synthetic pathway from pathways described in the prior art. For example, this synthetic pathway relies upon a novel stereospecific synthesis of an oxazoline intermediate, and a unique stereoselective addition of a formyl amide to the oxazoline.

The invention is also directed to novel analogs of Formulae VI and VII that possess unexpected biological activity. Lactacystin, clasto-lactacystin β-lactone, and analogs thereof possess biological activity as inhibitors of the proteasome. They can be used to treat conditions mediated directly by the function of the proteasome, such as muscle wasting, or mediated indirectly via proteins which are processed by the proteasome, such as the transcription factor NF-κB. The present invention is also directed to methods of inhibiting proteasome function or treating a condition that is mediated directly or indirectly by the function of the proteasome, by administering a compound of Formula VI or VII that possesses unexpectedly high activity in inhibiting the proteasome. In a preferred aspect of the invention, a pharmaceutical composition that includes a compound of Formula VI or Formula VII is administered to treat ischemic or reperfusion injury. For example, in a preferred embodiment said compounds can be used to treat, prevent or ameliorate neuronal loss following stroke.

Synthetic Processes

A first aspect of the present invention relates to processes for forming lactacystin and analogs thereof having Formula VI and clasto-lactacystin β-lactone and analogs thereof having Formula VII:

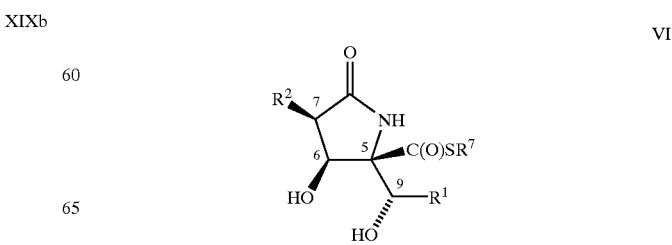

VI

-continued

VII

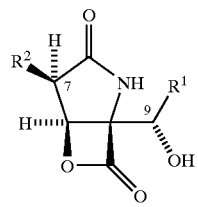

wherein $R^1$ is alkyl, alkenyl, alkynyl, cycloalkyl, aryl, alkaryl, aralkyl, where the ring portion of any of said aryl, aralkyl, or alkaryl can be optionally substituted;

$R^2$ is alkyl, cycloalkyl, aryl, alkaryl, aralkyl, alkoxy, hydroxy, alkoxyalkyl, or amido, where the ring portion of any of said aryl, aralkyl, or alkaryl can be optionally substituted; and $R^7$ is alkyl, aryl, aralkyl, alkaryl, wherein any of said alkyl, aryl, aralkyl or alkaryl can be optionally substituted.

The processes for forming these compounds rely upon formation of a common carboxylic acid intermediate of Formula V:

V

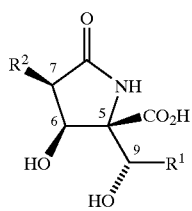

where $R^1$ and $R^2$ are as defined above for Formulae VI and VII. These steps include:

(a) deprotonating a substituted aryl or heteroaryl oxazoline of Formula I:

I

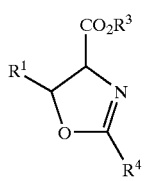

where $R^1$ is as defined above, and $R^3$ is alkyl, alkenyl, alkynyl, cycloalkyl, aryl, alkaryl, any of which can be optionally substituted; and $R^4$ is aryl or heteroaryl, either of which may be optionally substituted; by treating said substituted aryl or heteroaryl oxazoline with a strong base to form an enolate;

(b) transmetallating said enolate with a metal selected from the group consisting of titanium, aluminum, tin, zinc, magnesium and boron, and thereafter treating with a formyl amide of Formula XIV:

XIV

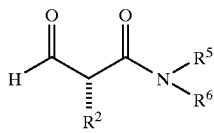

where $R^2$ is as defined above for Formulae VI and VII, and $R^5$ and $R^6$ are independently one of alkyl or alkaryl; or $R^5$ and $R^6$ when taken together with the nitrogen atom to which they are attached form a 5- to 7-membered heterocyclic ring, which may be optionally substituted, and which optionally may include an additional oxygen or nitrogen atom, to form an adduct of Formula II:

II

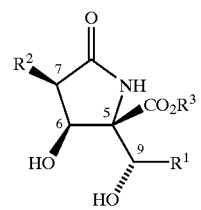

where $R^1$ through $R^6$ are as defined above;

c) catalytically hydrogenating said adduct of Formula II to form a γ-lactam of Formula IV:

IV

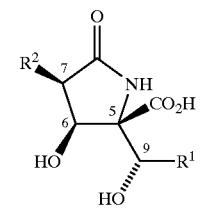

where $R^1$, $R^2$ and $R^3$ are as defined above;

d) saponifying said γ-lactam of Formula IV to form a lactam carboxylic acid of Formula V:

V

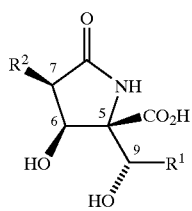

where $R^1$ and $R^2$ are as defined above.

The carboxylic acid intermediate of Formula V can be cyclized by treatment with a cyclizing reagent to form a clasto-lactacystin-β-lactone or analog thereof of Formula VII, which can be optionally further reacted with a thiol ($R^7SH$), such as N-acetylcysteine, to form lactacystin or an analog thereof having Formula VI.

Alternatively, the carboxylic acid intermediate of Formula V can be directly coupled to a thiol ($R^7SH$), such as N-acetylcysteine, to form lactacystin or an analog thereof having Formula VI.

A second aspect of the present invention relates to the formation of enantiomerically-enriched formyl amides of Formula XIV:

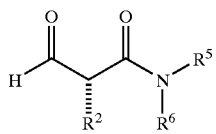

XIV wherein $R^2$, $R^5$ and $R^6$ are as defined above, said method comprising:

(a) deprotonating a compound of Formula VIII:

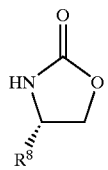

VIII where $R^8$ is isopropyl or benzyl, and thereafter acylating the resultant anion with $R^2CH_2COCl$ to form an acyloxazolidinone of Formula IX:

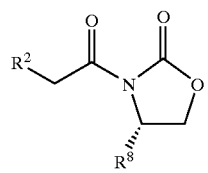

IX where $R^2$ and $R^8$ are as defined above;

(b) stereoselectively reacting the acyloxazolidinone of Formula IX with benzyloxymethyl chloride to form a protected alcohol of Formula X:

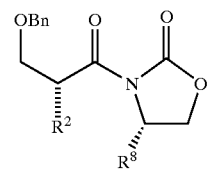

X where $R^2$ and $R^8$ as defined above;

(c) hydrolyzing the protected alcohol of Formula X to form a carboxylic acid of Formula XI:

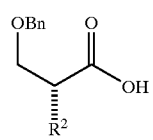

XI where $R^2$ is as defined above;

(d) coupling said acid of Formula XI with an amine $R^5R^6NH_2$ to provide an amide of Formula XII:

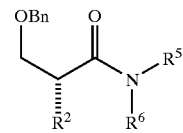

XII where $R^2$, $R^5$ and $R^6$ are as defined above;

(e) catalytically hydrogenating, the amide of Formula XII to form an alcohol of Formula XIII:

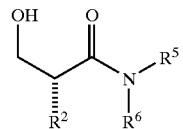

XIII where $R^2$, $R^5$ and $R_6$ are as defined above; and (f) oxidizing the resultant alcohol of Formula XIII to give a formyl amide of Formula XIV.

A third aspect of the invention relates to a process for forming a tri-substituted cis-oxazoline compound of Formula Ia:

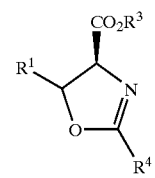

Ia wherein $R^1$ is alkyl, alkenyl, alkynyl, cycloalkyl, aryl, alkaryl, aralkyl, where the ring portion of any of said aryl, aralkyl, or alkaryl can be optionally substituted;

$R^3$ is alkyl, cycloalkyl, aryl, alkaryl, any of which can be optionally substituted; and $R^4$ is aryl or heteroaryl, either of which may be optionally substituted; said method comprising:

(a) asymmetrically dihydroxylating an alkene intermediate of Formula XV:

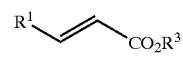

XV to form an optically active diol of Formula XVIa:

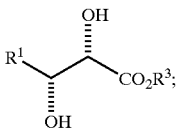

XVIa (b) reacting said optically active diol of Formula XVIa with an orthoester derived from an aromatic carboxylic acid under acid catalysis (Lewis or Brönsted acid) to give a mixed orthoester, and thereafter reacting the resulting mixed orthoester intermediate with a reagent selected from the group consisting of lower alkanoyl halides, hydrohalic acids (HX, where X is a halogen), acid chlorides, and halogen-containing Lewis acids (for example $BBr_3$, $SnCl_4$, $Ti(OR)_2Cl_2$, $Ti(OR)_3Cl$, $Me_3SiX$, where X is a halogen, and the like) in the presence of a base to form a derivative of Formula XVIIa:

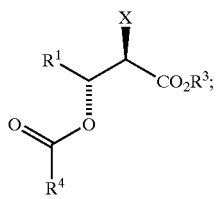

XVIIa wherein X is a halogen, preferably Cl, Br or I;

(c) reacting said derivative of Formula XVIIa with an alkali metal azide to form an azide of Formula XVIIIa:

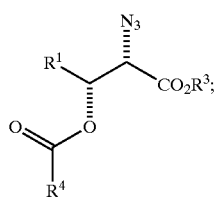

XVIIIa (d) catalytically hydrogenating said azide to form a compound of Formula XIXa:

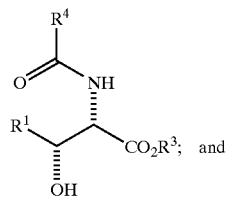

XIXa (e) subjecting the compound of Formula XIXa to ring closing conditions to form said substituted aryl- or heteroaryloxazoline of Formula I with inversion of configuration at the oxygen-substituted carbon to produce a cis-oxazoline of Formula Ia; wherein for each of Formulae XV, XVIa, XVIIa, XVIIIa and XIXa, $R^1$, $R^3$ and $R^4$ are as defined above for Formula I.

Alternatively, the third aspect of the invention relates to a process for forming a tri-substituted trans-oxazoline compound of Formula Ib comprising:

(a) asymmetrically dihydroxylating an alkene intermediate of Formula XV:

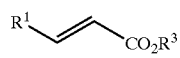

XV to form an optically active diol of Formula XVIb:

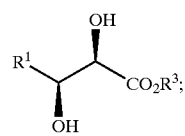

XVIb (b) reacting said optically active diol of Formula XVIb with an orthoester derived from an aromatic carboxylic acid under acid catalysis (Lewis or Brönsted acid) to give a mixed orthoester, and thereafter reacting the resulting mixed orthoester intermediate with a reagent selected from the group consisting of lower alkanoyl halides, hydrohalic acids (HX, where X is halogen), acid chlorides, and halogen-containing Lewis acids (for examples, $BBr_3$, $SnCl_4$, $Ti(OR)_2Cl_2$, $Ti(OR)_3Cl$, $Me_3SiX$, where X is a halogen, and the like) in the presence of a base to form a derivative of Formula XVIIb:

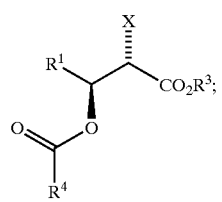

XVIIb wherein X is a halogen, preferably Cl, Br, or I;

(c) reacting said derivative of Formula XVIIb with an alkali metal azide to form an azide of Formula XVIIIb:

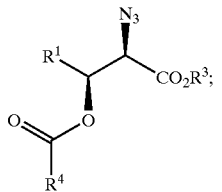

XVIIIb (d) catalytically hydrogenating said azide to form a compound of Formula XIXb:

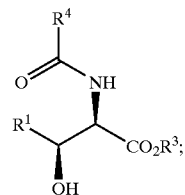

XIXb (e) subjecting the compound of Formula XIXb to ring closing conditions to form said substituted aryl- or heteroaryloxazoline of Formula Ib, wherein the ring closure reaction proceeds with retention of configuration at the oxygen-substituted carbon to produce a trans-oxazoline of Formula Ib; wherein for each of Formulae XV, XVI, XVII, XVII and XIX, $R^1$, $R^3$, and $R^4$ are as defined above for Formula I.

With respect to the processes described above, the following preferred values are applicable:

Preferred values of $R^1$ are $C_{1-12}$ alkyl, especially $C_{1-8}$ alkyl, $C_{1-8}$ cycloalkyl, especially $C_{3-6}$ cycloalkyl, $C_{2-8}$ alkenyl, $C_{2-8}$ alkynyl, $C_{6-14}$ aryl, especially $C_{6-10}$ aryl, $C_{6-10}$ ar($C_{1-6}$)alkyl or $C_{1-6}$ alk ($C_{6-10}$)aryl, where the ring portion of any of said aryl, aralkyl, or alkaryl can be optionally substituted. Substituents that can be optionally present on the aryl ring of an $R^1$ moiety include one or more, preferably one or two, of hydroxy, nitro, trifluoromethyl, halogen, $C_{1-6}$ alkyl $C_{6-10}$ aryl, $C_{1-6}$ alkoxy, $C_{1-6}$ aminoalkyl, $C_{1-6}$ aminoalkoxy, amino, $C_{2-6}$ alkoxycarbonyl, carboxy, $C_{1-6}$ hydroxyalkyl, $C_{2-6}$ hydroxyalkoxy, $C_{1-6}$ alkylsulfonyl, $C_{6-10}$ arylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, $C_{1-6}$ alkyl, $C_{1-6}$ hydroxyalkyl, $C_{6-10}$ aryl, $C_{6-10}$ aryl($C_{1-6}$) alkyl, $C_{1-6}$ alkylcarbonyl, $C_{2-6}$ carboxyalkyl, cyano, and trifluoromethoxy.

$R^1$ is more preferably one of $C_{1-8}$ alkyl such as ethyl, propyl or isopropyl; cycloalkyl, such as cyclohexyl; or $C_{6-10}$ aryl, such as phenyl. Most preferred is isopropyl.

Preferred values of $R^2$ are $C_{1-8}$ alkyl, $C_{3-8}$ cycloalkyl, especially $C_{3-6}$ cycloalkyl, $C_{1-8}$ alkoxy, $C_{2-8}$ alkenyl, $C_{2-8}$ alkynyl $C_{6-14}$ aryl, especially $C_{6-10}$ aryl, $C_{6-10}$ ar($C_{1-6}$)alkyl or $C_{1-6}$ alk($C_{6-10}$)aryl, where the ring portion of any of said aryl, aralkyl, or alkaryl can be optionally substituted with any of the substituents as described for $R^1$ above.

$R^2$ is more preferably $C_{1-4}$ alkyl, such as methyl, ethyl, propyl, or butyl; or $C_{1-4}$ alkoxy, such as methoxy, or ethoxy. Most preferred are methyl, ethyl and propyl, and butyl.

With respect to $R^3$, a variety of ester functionalities can be employed at this position. Preferred values are $C_{1-8}$ alkyl, $C_{3-8}$ cycloalkyl, especially $C_{4-7}$ cycloalkyl, $C_{2-8}$ alkenyl, $C_{2-8}$ alkynyl, $C_{6-14}$ aryl, especially $C_{6-10}$ aryl, $C_{6-10}$ ar($C_{1-6}$) alkyl or $C_{1-6}$ alk($C_{6-10}$)aryl, any of which can be optionally substituted. Substituents that can be optionally present on $R^3$ include one or more, preferably one or two, of the substituents as described for $R^1$ above.

$R^3$ is more preferably $C_{1-4}$ alkyl, $C_{6-10}$ aryl or $C_{6-10}$ ar($C_{1-6}$)alkyl. Most preferred are methyl, ethyl, tert-butyl and benzyl.

$R^4$ is preferably $C_{6-10}$ aryl, preferably phenyl, or a heteroaryl group selected from the group consisting of thienyl, benzo[b]thienyl, furyl, pyranyl, isobenzofuranyl, benzoxazolyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, or triazolyl. The phenyl or heteroaryl group can be optionally substituted by one or two of the substituents as described for $R^1$ above. Most preferred are phenyl, and phenyl substituted by halogen, $C_{1-6}$ alkyl, $C_{1-6}$ alkoxy, carboxy, amino, $C_{1-6}$ alkylamino and/or di($C_{1-6}$)alkylamino.

$R^5$ and $R^6$ are independently one of alkyl, aralkyl or alkaryl; or $R^5$ and $R^6$ when taken together with the nitrogen atom to which they are attached form a 5- to 7-membered heterocyclic ring, which can be optionally substituted, and which optionally can include an additional oxygen or nitrogen atom. Optional substituents are those listed above for $R^1$.

$R^5$ and $R^6$ are preferably $C_{1-6}$ alkyl, $C_{6-10}$ ar($C_{1-6}$)alkyl or $C_{1-6}$ alk($C_{6-10}$)aryl or together with the nitrogen atom to which they are attached form a 5- to 7-membered heterocycle which can be optionally substituted, and which optionally can include an additional oxygen or nitrogen atom. Most preferred values for $NR^5R^6$ are dimethylamino, diethylamino, pyrrolidino, piperidino, morpholino, oxazolidinone, and oxazolidinone substituted by halogen, $C_{1-6}$ alkyl, $C_{6-10}$ ar($C_{1-6}$)alkyl, $C_{1-6}$ alkoxy, carboxy, and/or amino.

$R^7$ is preferably $C_{1-8}$ alkyl, $C_{3-8}$ cycloalkyl, $C_{6-10}$ aryl, $C_{6-10}$ ar($C_{1-6}$)alkyl, $C_{1-6}$ alk($C_{6-10}$)aryl, any of which can be optionally substituted. Substituents that can be optionally present on either or both of the ring or chain portions of $R^7$ include one or more, preferably one or two, of the substituents as described for $R^1$ above. Preferably, $R^7$ together with the sulfur atom to which it is attached is cysteine or a derivative of cysteine such as N-acetyl cysteine, glutathione, and the like.

Scheme 1 is a general scheme for forming lactacystin and clasto-lactacystin-β-lactone analogs from substituted oxazoline starting materials.

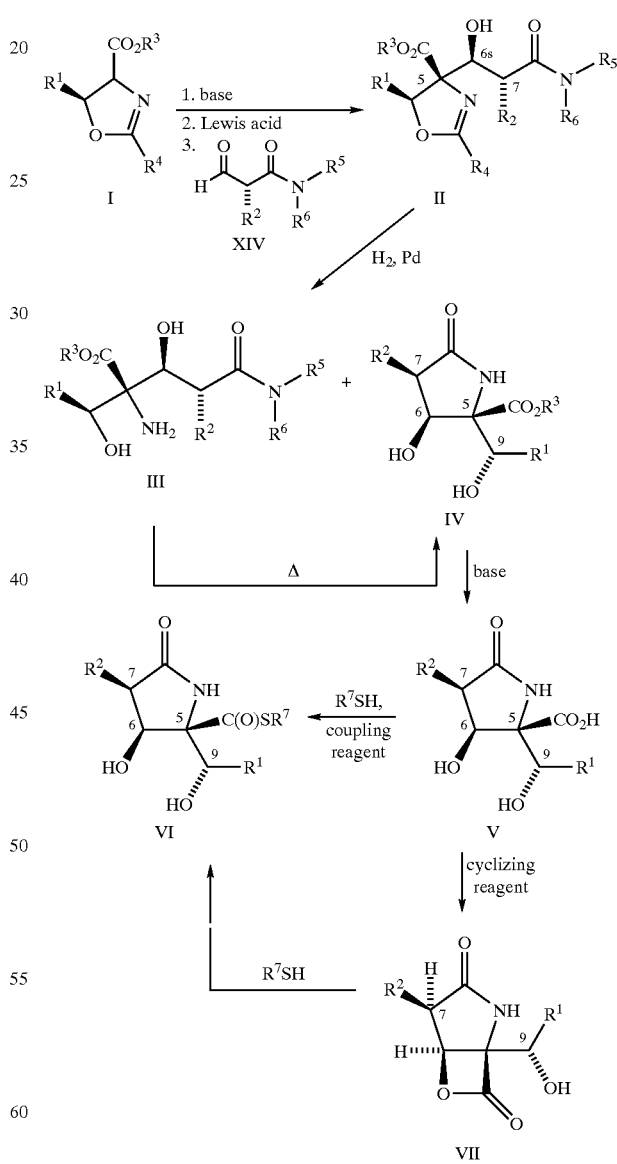

Scheme 1

The starting oxazoline I, which may be of either the cis (Ia) or trans (Ib) configuration, is deprotonated with a strong base to form the enolate. Examples of bases suitable for use in this reaction are organic bases, including hindered amide bases such as lithium diisopropylamide (LDA), lithium tetramethylpiperidide (LiTMP), lithium, sodium or potassium hexamethyldisilazide (LiHMDS, NaHMDS, KHMDS), or the like; or hindered alkyllithium reagents, such as sec-butyllithium, tert-butyllithium, or the like. The reaction is preferably conducted at reduced temperature in an ethereal solvent, such as diethyl ether, tetrahydrofuran (THF), or dimethoxyethane (DME). Reaction temperatures preferably range from about −100° C. to about −30° C., more preferably from −85° C. to −50° C., and most preferably from −85° C. to −75° C. The reaction temperature is important in determining the stereochemical outcome of the subsequent addition to the aldehyde, with lower temperatures providing better selectivity.

The deprotonation step is followed by transmetallating said enolate with a metal selected from the group consisting of titanium, aluminum, tin, zinc, magnesium and boron. Preferred reagents for this step include titanium or aluminum Lewis acids, for example Me$_2$AlCl or (i-PrO)$_3$TiCl or a mixture of the two. Preferably, between one and three molar equivalents of the Lewis acid are used, more preferably between two and three equivalents, and most preferably about 2.2–2.3 equivalents. Subsequent treatment of the enolate with a formyl amide (XIV) affords the adduct II. Excess aldehyde is washed away with sodium bisulfite solution, and the crude material is carried forward to the next step without further purification. The use of 2.2–2.3 equivalents of Me$_2$AlCl results in selective formation of the (6S)-product (lactacystin numbering), in a ratio generally better than about 10:1, whereas the use of 1 equivalent of Me$_2$AlCl results in selective formation of the (6R)-product, in a ratio of about 5:1.

Catalytic hydrogenolysis of the adduct II, as a mixture of (6S)- and (6R)-epimers, affords the desired γ-lactam (IV), sometimes as a mixture with the aminodiol III:

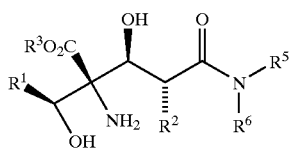

III

Useful catalysts for this reaction include palladium black, palladium on activated carbon, palladium hydroxide on carbon, or the like. Organic solvents suitable for use in this reaction include lower alkanols such as methanol, ethanol, or isopropanol, lower alkanoates such as ethyl acetate, lower alkanoic acids such as acetic acid, or mixtures thereof. The reaction is conducted under an atmosphere of hydrogen, at pressures ranging from about 15 to about 100 p.s.i., more preferably from about 30 to about 50 p.s.i. Alternatively, transfer hydrogenation procedures (R. A. W. Johnstone et al., *Chem. Rev.* 85:129 (1985)) may be used, in which the adduct II is treated at atmospheric pressure with a catalyst and a hydrogen donor.

Upon heating of the crude product mixture, the aminodiol III is converted to the γ-lactam IV, which can then be isolated in approximately 60–75% overall yield from II. The heating step is conveniently carried out by first filtering off the catalyst used in the hydrogenation step and then heating the filtrate to reflux. When no aminodiol III is present in the crude product mixture, the heating step is omitted. Ester saponification, followed by cyclization, affords the β-lactone VII in 40–90% yield, and generally in greater than 60% yield. Cyclization can be effected with coupling reagents known in the art, including aryl sulfonyl chlorides, benzotriazol-1-yloxytris(dimethylamino)phosphonium hexafluorophosphate (BOP reagent), O-(1H-benzotriazol-1-yl)-N,N,N',N'-tetramethyluronium tetrafluoroborate (TBTU), alkyl, aryl or alkenyl chloroformates, and the like. Isopropenyl chloroformate is a preferred reagent for this step, since all byproducts are volatile and chromatographic purification of the product is not necessary.

clasto-Lactacystin β-lactone can be converted to lactacystin by treatment of the β-lactone with N-acetylcysteine according to the reported procedure (Corey et al., *Tetrahedron Lett.* 34:6977 (1993)). Reactions of the β-lactone VII with other thiols proceed analogously. Alternatively, lactacystin analogs are prepared by coupling the carboxylic acid intermediate V with a thiol to form the corresponding thiolester VI. The method of this invention is therefore useful for synthesis of both lactacystin and clasto-lactacystin β-lactone, as well as analogs thereof.

The enantiomerically-enriched formyl amides XIV employed in the aldol reaction are new. They can be prepared according to a representative reaction sequence such as that depicted in Scheme 2. For purposes of the present invention, the term "enantiomerically-enriched" means that one enantiomer is present in excess relative to the other; that is, one enantiomer represents greater than 50% of the mixture. The term "stereoselective" is used to mean that a synthesis or reaction step produces one enantiomer or diastereomer in excess relative to the other enantiomer or to other diastereomer(s).

Scheme 2

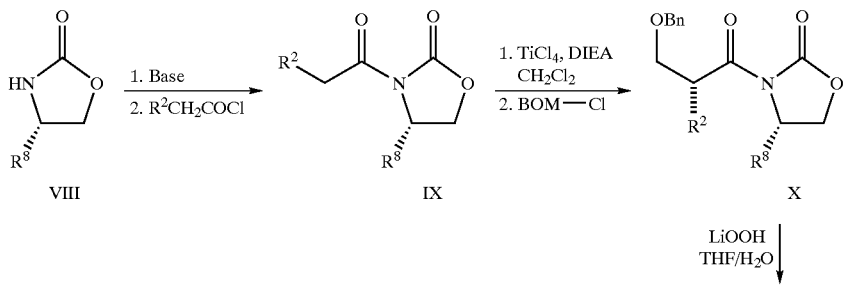

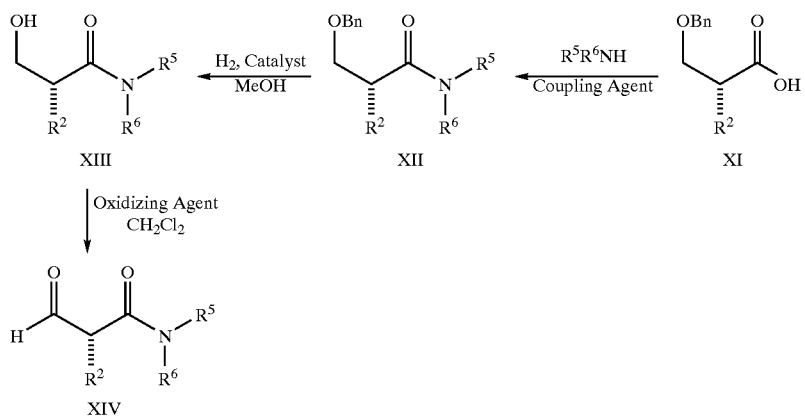

Acylation of the anion of (S)-(−)-4-benzyl-2-oxazolidinone (VIIIa) or (S)-(−)-4-isopropyl-2-oxazolidinone (VIIIb) (where $R^8$ is benzyl or isopropyl) affords the acyloxazolidinone IX in greater than 80% yield. Subsequent stereoselective benzyloxymethylation (Evans et al., *J. Am. Chem. Soc.* 112:8215 (1990)) gives the protected alcohol X in greater than 80% yield, provided that the benzyl chloromethyl ether is freshly prepared (Connor et al., *Organic Syntheses* 52:16 (1974)). Peroxide mediated hydrolysis affords the acid XI, which is coupled with an amine to provide the amide XII, generally in greater than 50% overall yield. Benzyl group hydrogenolysis, followed by oxidation of the resultant alcohol (XIII) then affords the formyl amide XIV in 80–85% yield. Pearlmans catalyst (Pd(OH)$_2$) is preferably used for the hydrogenolysis step. The final oxidation step is best accomplished with the periodinane reported by Dess and Martin, *J. Org. Chem.* 48:4156 (1983) or with 2,2,6,6-tetramethyl-1-piperidinyloxy (TEMPO) free radical, and buffered hypochlorite in the presence of bromide ion (*J. Org. Chem.* 50:4888 (1985); *Org. Synth. Coll.* 8:367 (1993)). Other mild oxidants such as tetrapropyl-ammonium perruthenate (TPAP) can also be used. The formyl amide XIV can be shown to be enantiomerically pure by reducing the aldehyde with sodium borohydride and converting the resultant alcohol to the corresponding Mosher ester using R-(+)-α-methoxy-α-(trifluoromethyl) phenylacetyl chloride (Dale et al., *J. Org. Chem.* 34:2543 (1969)). $^1$H NMR analysis at 300 MHz reveals a single diastereomer. The aldehydes prepared according to Scheme 2 are configurationally stable, showing no signs of enantiomeric deterioration after one week, when stored at 0° C. The aldehyde is also configurationally stable under the conditions of the aldol reaction, and the adduct II is formed without epimerization of the substituent $R^2$ at C(7).

The synthetic methods will work with any substituent at $R^1$ that is stable to strong base and to hydrogenation. Isopropyl is the preferred substituent for good proteasome inhibiting activity of the final product.

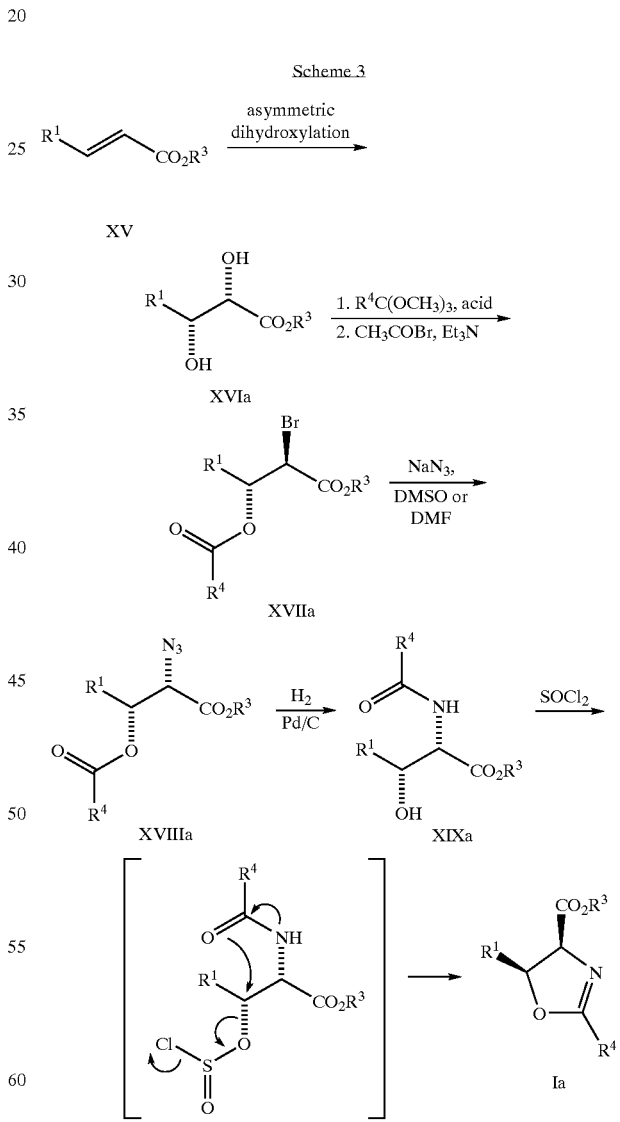

The invention also relates to a new route to form the oxazoline starting material I. The overall synthesis includes five steps (Scheme 3) and affords the cis-substituted oxazoline Ia, which is thereafter employed in the method described above. The first step depicted in Scheme 3 is Sharpless asymmetric dihydroxylation (Sharpless et al., *J. Org. Chem.* 57:2768 (1992); Kolb et al., *Chem. Rev.* 94:2483 (1994); Shao and Goodman, *J. Org. Chem.* 61:2582 (1996)) of the alkene XV. If not commercially available, the alkene XV is prepared by Wittig condensation between the aldehyde and carboethoxymethylene triphenylphosphorane (Hale et al., *Tetrahedron* 50:9181 (1994)). Other olefination procedures are also known in the art. The dihydroxylation reaction is preferably conducted with AD-mix-β (Aldrich Chemical Co.) in the presence of methane sulfonamide and stereoselectively affords the diol XVIa, as predicted by the Sharpless face-selection rule. On a large scale, the dihydroxylation reaction is preferably conducted using N-methylmorpholine-N-oxide (NMO) as the reoxidant in place of $K_3Fe(CN)_6$ present in AD-mix-β. Although proceeding with somewhat lower enantioselectivity, this procedure allows more concentrated reaction mixtures and greatly simplifies the workup. The enantiomeric purity of the product can be enhanced by recrystallization.

In the next step, the diol XVIa is treated with an orthoester under Lewis or Brönsted acid catalysis to give a mixed orthoester, which is converted in situ to the haloester XVIIa by treatment with an acyl halide (Haddad et al., *Tetrahedron Lett.* 37:4525 (1996)). Although acyl halides, especially acetyl halides are preferred for this reaction, other acid halides such as HCl, HBr, HI, $Me_3SiCl$, $Me_3SiI$, $Me_3SiBr$ and the like may be used. Halogen-containing Lewis acids of the formula $ML_nX$, such as $BBr_3$, $SnCl_4$, $Ti(OR)_2Cl_2$, $Ti(OR)_3Cl$, and the like can also be used. In the previous formula, M is a metal selected from the group consisting of B, Ti, Sn, Al, Zn, and Mg; L is any suitable ligand for the metal, preferably an alkoxide or halogen group; n is an integer that results in a stable complex, and X is a halogen. Preferably acetyl bromide is used to produce the haloester XVIIa. Preferably the orthoester employed in this reaction is derived from an aromatic or heteroaromatic carboxylic acid. More preferably, the orthoester is derived from benzoic acid, e.g., trimethyl orthobenzoate. The use of boron trifluoride etherate as the Lewis acid catalyst in the formation of the mixed orthoester is preferred, but other acids, such as HBr, $SnCl_4$, $TiCl_4$, $BBr_3$, and the like, can also be used.

After workup, the crude halide XVIIa is converted to the azide XVIIIa by treatment with an alkali metal azide in a polar aprotic organic solvent, such as dimethyl sulfoxide (DMSO) or N,N-dimethyl formamide (DMF). Catalytic hydrogenation of the azide XVIIIa over a palladium catalyst in ethyl acetate proceeds with concomitant migration of the aroyl group (Wang et al., *J. Org. Chem.* 59:5014 (1994)) to afford the hydroxyamide XIXa.

Treatment of XIXa with thionyl chloride in methylene chloride effects ring closure with inversion of configuration at the hydroxyl-substituted carbon atom to produce the cis-substituted oxazoline starting material Ia. Other reagents suitable for use in this reaction include sulfuryl chloride, phosphorous trichloride, phosphorous oxychloride, and (methoxycarbonylsulfamoyl)-triethylammonium hydroxide, inner salt (Burgess reagent). Treatment of XIXa under Mitsunobu conditions (Mitsunobu, *Synthesis*: 1 (1981)) will also effect a ring closure. The oxazoline ring oxygen atom is destined to become the C(9)-hydroxyl group in the final products VI and VII. Under equilibrating conditions (sodium methoxide, methanol), the cis-oxazoline (Ia) is converted to the trans-oxazoline (Ib) by inversion of configuration of the ester substituent, with the configuration of the $R^1$ substituent remaining fixed. The cis- and trans-oxazolines can both be used in the method depicted in Scheme 1, with equivalent results.

In an alternative route to form the oxazoline starting material I, p-toluenesulfonic acid (p-TsOH) is used to effect ring closure (Scheme 4). In this case, ring closure proceeds with retention of configuration at the hydroxyl-substituted carbon atom to afford the trans-oxazoline (Ib). In order to obtain the proper stereochemistry at C(9) of the final product, the chiral ligand employed in the dihydroxylation reaction must be selected so as to provide the opposite face selectivity from that depicted in Scheme 3. For example, AD-mix-α is used in place of AD-mix-β. All other steps in the sequence proceed analogously to those described for the synthesis of the cis-oxazoline Ia.

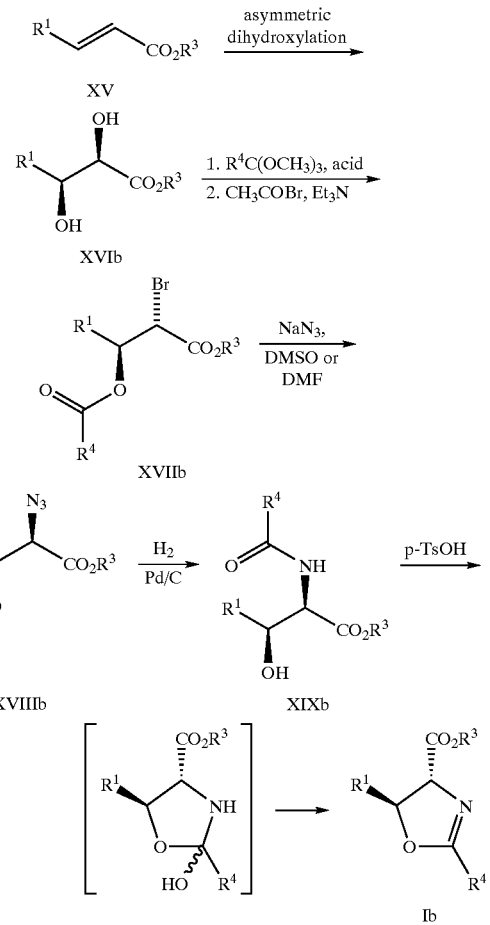

Compounds

Many of the compounds described above are novel compounds; the novel compounds are also claimed.

Fourth, fifth and sixth aspects of the invention relate to lactacystin analogs that can be made by the synthetic routes described herein; to pharmaceutical compositions including such compounds; and to methods of treating a subject having a condition mediated by proteins processed by the proteasome by administering to a subject an effective amount of a pharmaceutical composition disclosed herein. These methods include treatments for Alzheimers disease, cachexia, cancer, inflammation (e.g., inflammatory responses associated with allergies, bone marrow or solid organ transplantation, or disease states, including but not limited to arthritis, multiple sclerosis, inflammatory bowel disease and parasitic diseases such as malaria), psoriasis, restenosis, stroke, and myocardial infarction.

The compounds of Formulae VI and VII disclosed herein are highly selective for the proteasome, and do not inhibit other proteases such as trypsin, α-chymotrypsin, calpain I, calpain II, papain, and cathepsin B.

As disclosed by Fenteany et al. (WO 96/32105), hereby incorporated by reference in its entirety, lactacystin, clasto-lactacystin β-lactone, and analogs thereof possess biological activity as inhibitors of the proteasome. They can be used to treat conditions mediated directly by the function of the proteasome, such as muscle wasting, or mediated indirectly via proteins which are processed by the proteasome, such as the transcription factor NF-κB. The compounds prepared by the methods of this invention can also be used to determine whether a cellular, developmental, or physiological process or output is regulated by the proteolytic activity of the proteasome.

Those compounds that possess unexpected proteasome function-inhibiting activity are compounds of Formulae VI and VII:

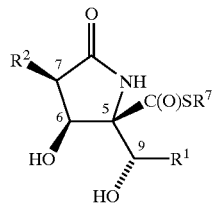

VI

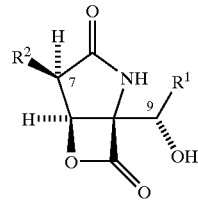

VII or a salt thereof, wherein:

$R^1$ is $C_{1-12}$ alkyl, $C_{3-8}$ cycloalkyl, $C_{2-8}$ alkenyl, $C_{2-8}$ alkynyl, $C_{2-8}$ alkynyl, $C_{6-14}$ aryl, $C_{6-10}$ ar($C_{1-6}$)alkyl or $C_{1-6}$ alk($C_{6-10}$)aryl;

$R^2$ is $C_{2-6}$ alkyl; and $R^7$ is $C_{1-8}$ alkyl, $C_{3-8}$ cycloalkyl, $C_{6-10}$ aryl, $C_{6-10}$ ar($C_{1-6}$)alkyl, $C_{1-6}$ alk($C_{6-10}$)aryl, any of which can be optionally substituted. Substituents that can be optionally present on either or both of the ring or chain portions of $R^7$ include one or more, preferably one or two, of the substituents as described for $R^1$ above.

Preferred compounds are those where $R^1$ is $C_{1-4}$ alkyl, more preferably isopropyl. $R^2$ is preferably ethyl, n-propyl, n-butyl or isobutyl. Preferably, $R^7$ together with the sulfur atom to which it is attached is cysteine or a derivative of cysteine such as N-acetyl cysteine, glutathione, and the like.

A seventh aspect of the present invention is directed to enantiomerically-enriched formyl amides of Formula XIV:

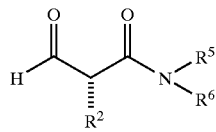

XIV or salts thereof, wherein $R^2$ is $C_{1-8}$ alkyl, $C_{3-8}$ cycloalkyl, $C_{2-8}$ alkenyl, $C_{2-8}$ alkynyl, $C_{6-14}$ aryl, $C_{6-10}$ ar($C_{1-6}$)alkyl or $C_{1-6}$ alk($C_{6-10}$)aryl; and $R^5$ and $R^6$ are independently $C_{1-6}$ alkyl, $C_{6-10}$ ar($C_{1-6}$)alkyl or $C_{1-6}$ alk($C_{6-10}$)aryl, or together with the nitrogen atom to which they are attached form a 5- to 7-membered heterocycle which can be optionally substituted, and which optionally can include an additional oxygen or nitrogen atom.

Preferred compounds are those where $R^2$ is $C_{2-6}$ alkyl.

An eighth aspect of the present invention is directed to compounds of Formulae II and III:

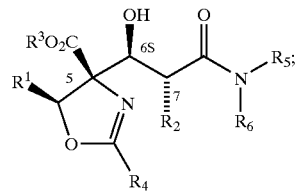

II

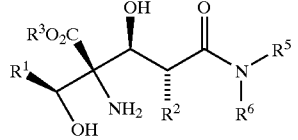

III or salts thereof wherein $R^1$ is alkyl, alkenyl, alkynyl, cycloalkyl, aryl, alkaryl, aralkyl, where the ring portion of any of said aryl, aralkyl, or alkaryl can be optionally substituted;

$R^2$ is alkyl, cycloalkyl, aryl, alkaryl, aralkyl, alkoxy, hydroxy, alkoxyalkyl, or amido, where the ring portion of any of said aryl, aralkyl, or alkaryl can be optionally substituted;

$R^3$ is alkyl, alkenyl, alkynyl, cycloalkyl, aryl, alkaryl, any of which can be optionally substituted;

$R^4$ is optionally substituted aryl or optionally substituted heteroaryl; and $R^5$ and $R^6$ are independently one of alkyl or alkaryl; or $R^5$ and $R^6$ when taken together with the nitrogen atom to which they are attached form a 5- to 7-membered heterocyclic ring, which can be optionally substituted, and which optionally include an additional oxygen or nitrogen atom. Most preferred values for $NR^5R^6$ are dimethylamino, diethylamino, pyrrolidino, piperidino, morpholino, oxazolidinone, and oxazolidinone substituted by halogen, $C_{1-6}$ alkyl, $C_{6-10}$ ar($C_{1-6}$)alkyl, $C_{1-6}$ alkoxy, carboxy, and/or amino.

Preferred compounds of Formulae II and III are those wherein:

$R^1$ is $C_{1-12}$ alkyl, $C_{3-8}$ cycloalkyl, $C_{2-8}$ alkenyl, $C_{2-8}$ alkynyl, $C_{6-14}$ aryl, $C_{6-10}$ ar($C_{1-6}$)alkyl or $C_{1-6}$ alk($C_{6-10}$)aryl, where the ring portion of any of said aryl, aralkyl, or alkaryl can be optionally substituted;

$R^2$ is $C_{1-8}$ alkyl, $C_{3-8}$ cycloalkyl, $C_{2-8}$ alkenyl, $C_{2-8}$ alkynyl, $C_{6-14}$ aryl, $C_{6-10}$ ar($C_{1-6}$)alkyl or $C_{1-6}$ alk($C_{6-10}$)aryl, where the ring portion of any of said aryl, aralkyl, or alkaryl can be optionally substituted;

$R^3$ is $C_{1-8}$ alkyl, $C_{3-8}$ cycloalkyl, $C_{2-8}$ alkenyl, $C_{2-8}$ alkynyl, $C_{6-14}$ aryl, $C_{6-10}$ ar($C_{1-6}$)alkyl or $C_{1-6}$ alk($C_{6-10}$)aryl, any of which can be optionally substituted;

$R^4$ is optionally substituted $C_{6-10}$ aryl, or an optionally substituted heteroaryl group selected from the group consisting of thienyl, benzo[β]thienyl, furyl, pyranyl, isobenzofuranyl, benzoxazolyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, or triazolyl; and $R^5$ and $R^6$ are independently $C_{1-6}$ alkyl, $C_{6-10}$ ar($C_{1-6}$)alkyl or $C_{1-6}$ alk($C_{6-10}$)aryl, or together with the nitrogen atom to which they are attached form a 5- to 7-membered heterocycle which can be optionally substituted, and which optionally can include an additional oxygen or nitrogen atom. Most preferred values for $NR^5R^6$ are dimethylamino, diethylamino, pyrrolidino, piperidino, morpholino, oxazolidinone, and oxazolidinone substituted by halogen, $C_{1-6}$ alkyl, $C_{6-10}$ ar($C_{1-6}$)alkyl, $C_{1-6}$ alkoxy, carboxy, and/or amino.

A ninth aspect of the present invention is directed to compounds of Formulae XVIIa, XVIIb, XVIIIa, XVIIIb, XIXa or XIXb:

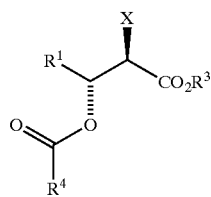

XVIIa

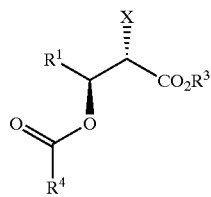

XVIIb

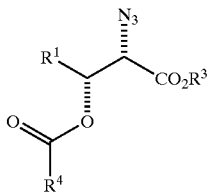

XVIIIa

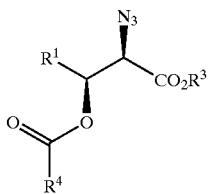

XVIIIb

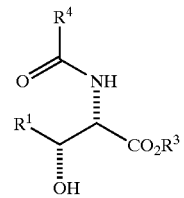

XIXa

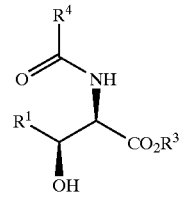

XIXb or salts thereof, wherein $R^1$ is alkyl, alkenyl, alkynyl, cycloalkyl, aryl, alkaryl, aralkyl, where the ring portion of any of said aryl, aralkyl, or alkaryl can be optionally substituted;

$R^3$ is alkyl, alkenyl, alkynyl, cycloalkyl, aryl, alkaryl, any of which can be optionally substituted; and $R^4$ is optionally substituted aryl or optionally substituted heteroaryl.

Preferred compounds of Formulae XVII, XVIII or XIX are those wherein $R^1$ is $C_{1-12}$ alkyl, $C_{3-8}$ cycloalkyl, $C_{2-8}$ alkenyl, $C_{2-8}$ alkynyl $C_{6-14}$ aryl, $C_{6-10}$ ar($C_{1-6}$)alkyl or $C_{1-6}$ alk($C_{6-10}$)aryl, where the ring portion of any of said aryl, aralkyl, or alkaryl can be optionally substituted;

$R^3$ is $C_{1-8}$ alkyl, $C_{3-8}$ cycloalkyl, $C_{2-8}$ alkenyl, $C_{2-8}$ alkynyl, $C_{6-4}$ aryl, $C_{6-10}$ ar($C_{1-6}$)alkyl or $C_{1-6}$ alk($C_{6-10}$)aryl, any of which can be optionally substituted; and $R^4$ is optionally substituted $C_{6-10}$ aryl, or an optionally substituted heteroaryl group selected from the group consisting of thienyl, benzo[b]thienyl, furyl, pyranyl, isobenzofuranyl, benzoxazolyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, or triazolyl.

Definitions

The term "alkyl" as employed herein includes both straight and branched chain radicals of up to 12 carbons, preferably 1–8 carbons, such as methyl, ethyl, propyl, isopropyl, butyl, t-butyl, isobutyl, pentyl, hexyl, isohexyl, 1-ethylpropyl, heptyl, 4,4-dimethylpentyl, octyl, 2,2,4-trimethylpentyl, nonyl, decyl, undecyl and dodecyl.

The term "substituted alkyl" as employed herein, includes alkyl groups as defined above that have one, two or three halo, hydroxy, nitro, trifluoromethyl, halogen, $C_{1-6}$ alkyl, $C_{6-10}$ aryl, $C_{1-6}$ alkoxy, $C_{1-6}$ aminoalkyl, $C_14$ aminoalkoxy, amino, $C_{2-6}$ alkoxycarbonyl, carboxy, $C_{1-6}$ hydroxyalkyl, $C_{2-6}$ hydroxyalkoxy, $C_{1-6}$ alkylsulfonyl, $C_{6-10}$ arylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylcarbonyl, $C_{2-6}$ carboxyalkyl, cyano, and trifluoromethoxy and/or carboxy substituents.

The term "cycloalkyl" as employed herein includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, $C_{1-6}$ alkyl, $C_{1-6}$ alkoxy and/or hydroxy group.

The term "heteroaryl" as employed herein refers to groups having 5 to 14 ring atoms, preferably 5, 6, 9 or 10 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, tetrazolyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "alkaryl" or "alkylaryl" as employed herein by itself or as part of another group refers to an aryl group as discussed above having a $C_{1-6}$ alkyl substituent, such as toluyl, ethylphenyl, or methylnaphthyl.

The term "optionally substituted" when used with respect to aryl, aralkyl, alkaryl or 5-, 6-, 9- or 10-membered heteroaryl groups means that the ring portion of said groups can be optionally substituted by one or two substituents independently selected from $C_{1-6}$ alkyl, $C_{3-8}$ cycloalkyl, $C_{1-6}$ alkyl($C_{3-8}$)cycloalkyl, $C_{2-8}$ alkenyl, $C_{2-8}$ alkynyl, cyano, amino, $C_{1-6}$ alkylamino, di($C_{1-6}$)alkylamino, benzylamino, dibenzylamino, nitro, carboxy, carbo($C_{1-6}$)alkoxy, trifluoromethyl, halogen, $C_{1-6}$ alkoxy, $C_{6-10}$ aryl, $C_{6-10}$ aryl($C_{1-6}$)alkyl, $C_{6-10}$ aryl($C_{1-6}$)alkoxy, hydroxy, $C_{1-6}$ alkylthio, $C_{1-6}$ alkylsulfinyl, $C_{1-6}$ alkylsulfonyl, $C_{6-10}$ arylthio, $C_{6-10}$ arylsulfinyl, $C_{6-10}$ arylsulfonyl, $C_{6-10}$ aryl, $C_{1-6}$ alkyl($C_{6-10}$)aryl, and halo($C_{6-10}$)aryl.

The term "alkoxy" refers to the above alkyl groups linked to oxygen.

The term "halogen" or "halo" as employed herein by itself or as part of another group refers to chlorine, bromine, fluorine or iodine.

The term "amido" as employed herein refers to formylamino, alkylcarbonylamino or arylcarbonylamino.

Uses

Pharmacological data for clasto-lactacystin β-lactone analogs prepared by the methods of this invention are provided in Table 1. These compounds are all irreversible inactivators of the 20S proteasome, acylating the N-terminal threonine residue of the X/MB1 subunit. The value $K_{obs}/[I]$ is a measure of the rate of enzyme inactivation. Several compounds show improved activity, i.e., more rapid rates of inactivation, when compared to clasto-lactacystin β-lactone itself (2). The compound that is most potent in the enzyme assay is the 7-methoxy derivative 3f. However, when assayed in cell culture, 3f is less potent than 2.

The lactone ring is subject to nucleophilic attack not only by the threonine residue of the proteasome X/MB1 subunit, but also by water. Hydrolysis results in formation of the hydroxy acid V, which is not active as an inhibitor of the proteasome. Relative potency in cell culture is a composite of many factors, including enzyme potency, cell penetration, and hydrolysis rate. Although more potent than 2 against the enzyme, 3f is also more rapidly hydrolyzed, resulting in much weaker activity in cell culture. By contrast, the analogs 3a–3d show unexpectedly improved potency not only in the enzyme assay, but also in cell culture.

The disclosed compounds are used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins involved in cellular regulation (e.g., cell cycle, gene transcription, and metabolic pathways), intercellular communication, and the immune response (e.g., antigen presentation). Specific examples include β-amyloid protein and regulatory proteins such as cyclins and transcription factor NF-κB. Treating as used herein includes reversing, reducing, or arresting the symptoms, clinical signs, and underlying pathology of a condition in a manner to improve or stabilize the subject's condition.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles.

Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736 (1994).

Embodiments of the invention therefore encompass methods for reducing the rate of muscle protein degradation in a cell, and reducing the rate of intracellular protein degradation. Each of these methods includes the step of contacting a cell (in vivo or in vitro, e.g., a muscle in a subject) with an effective amount of a compound (e.g., pharmaceutical composition) of a formula disclosed herein.

Proteasome inhibitors block processing of ubiquitinated NF-κB in vitro and in vivo. Proteasome inhibitors also block IκB-α degradation and NF-κB activation. (Palombella, et al.; and Traenckner, et al., *EMBO J*. 13:5433–5441 (1994)). One embodiment of the invention is a method for inhibiting IκB-α degradation, including contacting the cell with a compound of a formula described herein. A further embodiment is a method for reducing the cellular content of NF-κB in a cell, muscle, organ, or subject, including contacting the cell, muscle, organ, or subject with a compound of a formula described herein. Additional embodiments encompass methods for treating inflammatory responses associated with allergies, bone marrow or solid organ transplantation, or disease states, including but not limited to arthritis, inflammatory bowel disease, asthma, and multiple sclerosis by administering a compound of a formula disclosed herein. A preferred embodiment of the invention is directed to treating asthma by administering a compound of Formula VI or Formula VII, most preferably compound 3b.

Proteasome inhibitors are also useful for treatment of ischemic or reperfusion injury, particularly for preventing or reducing the size of infarct after vascular occlusion such as occurs during a stroke or heart attack, as described in Brand, U.S. Pat. No. 6,271,199 (2001). Proteasome inhibitors also block proteasome-dependent transformation of protozoan parasites (Gonzalez et al., *J. Exp. Med.* 184:1909 (1996). Further embodiments of the invention therefore encompass methods for treating an infarct or a protozoan parasitic disease by administering a compound of a formula disclosed herein. In a preferred aspect of the invention, a compound of Formula VI or Formula VII is administered to prevent or reduce the size of the infarct after vascular occlusion. Said compounds can be administered from about 0 to about 10 hours from the occurrence of a stroke in order to treat or reduce neuronal loss following an ischemic event. Compound 3b is the most preferred compound in this aspect of the invention.

Proteasome inhibitors also block degradation of cell cycle regulatory proteins, such as cyclins and cyclin-dependent kinase inhibitors, and tumor suppressor proteins, such as p53. Other embodiments of the invention therefore encompass methods for blocking the cell cycle and for treating cell proliferative diseases such as cancer, psoriasis, and restenosis with a compound of a formula described herein.

The term "inhibitor" is meant to describe a compound that blocks or reduces the activity of an enzyme (e.g., the proteasome, or the X/MB1 subunit of the 20S proteasome). An inhibitor may act with competitive, uncompetitive, or noncompetitive inhibition. An inhibitor may bind reversibly or irreversibly, and therefore the term includes compounds which are suicide substrates of an enzyme. An inhibitor may modify one or more sites on or near the active site of the enzyme, or it may cause a conformational change elsewhere on the enzyme.

Amounts and regimens for the administration of proteasome inhibitors and compositions of the invention can be determined readily by those with ordinary skill in the clinical art. Generally, the dosage of the composition of the invention will vary depending upon considerations such as: type of composition employed; age; health; medical conditions being treated; kind of concurrent treatment, if any, frequency of treatment and the nature of the effect desired; extent of tissue damage; gender; duration of the symptoms; and, counter indications, if any, and other variables to be adjusted by the individual physician. A desired dosage can be administered in one or more applications to obtain the desired results. Pharmaceutical compositions containing the proteasome inhibitors of the invention can be provided in unit dosage forms.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for a proteosome-mediated condition such as a stroke or asthma. For intramuscular injection, the dose is generally about one-half of the oral dose.

In the method of prevention or reduction of infarct size the compound can be administered by intravenous injection at a dose of about 0.01 to about 10 mg/kg, preferably about 0.025 to about 1 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates. For use in treating stroke, it is preferred that a single dosage be administered, 0 to about 10 hours post-event, preferably 0 to about 6 hours post-event.

The following examples are illustrative, but not limiting, of the method and compositions of the present invention. Other suitable modifications and adaptations of the variety of conditions and parameters normally encountered and obvious to those skilled in the art are within the spirit and scope of the invention.

The preparation of formyl amides XIV according to the synthetic scheme depicted in scheme 2 as exemplified in Examples 1–6.

EXAMPLE 1

Acyl Oxazolidinones (IX)

a. Acyl oxazolidinone IXb ($R^2$=n-Pr; $R^8$=$CH_2Ph$)

A cooled (−78° C.) solution of (S)-(−)-4-benzyl-2-oxazolidinone (4.0 g, 22.6 mmol) in 75 mL anhydrous THF was treated with a 2.5 M solution of n-BuLi in hexane (9.1 mL, 22.6 mmol) over 15 min. After 5 min, neat valeryl chloride (2.95 mL, 24.9 mmol) was added dropwise and the mixture was stirred for another 45 min. at −78° C. The mixture was then allowed to reach room temperature, stirred for another 90 min, and then treated with 50 mL saturated $NH_4Cl$ solution. Dichloromethane (50 mL) was then added and the organic layer was washed with brine (2×30 mL), dried over $MgSO_4$ and concentrated in vacuo. This afforded 5.94 g (100%) of the desired acyl oxazolidinone IXb as a clear colorless oil. $^1H$ NMR (300 MHz, $CDCl_3$) δ7.36–7.20 (m, 5H), 4.71–4.64 (m, 1H), 4.23–4.14 (m, 1H), 3.40 (dd, J=13.3, 3.2 Hz, 1H), 3.04–2.84 (m, 2H), 2.77 (dd, J=13.3, 9.6 Hz, 1H), 1.74–1.63 (m, 2H), 1.46–1.38 (m, 2H), 0.96 (t, J=7.3 Hz, 3H).

b. Acyl oxazolidinone IXa ($R^2$=Et; $R^8$=$CH_2Ph$)

By a procedure analogous to that described for preparing acyl oxazolidinone IXb, the lithium anion of (S)-(−)-4-benzyl-2-oxazolidinone was treated with butyryl chloride to provide acyl oxazolidinone IXa in 94% yield. $^1H$ NMR (300 MHz, $CDCl_3$) δ7.37–7.20 (m, 5H), 4.68 (ddd, J=13.1, 7.0, 3.4 Hz, 1H), 4.23–4.13 (m, 2H), 3.30 (dd, J=13.3, 9.6 Hz, 1H), 3.02–2.82 (m, 2H), 2.77 (dd, J=13.3, 9.6 Hz, 1H), 1.73 (q, J=7.3 Hz, 2H), 1.01 (t, J=7.3 Hz, 3H).

c. Acyl oxazolidinone IXc ($R^2$=n-Bu; $R^8$=$CH_2Ph$)

By a procedure analogous to that described for preparing acyl oxazolidinone IXb, the lithium anion of (S)-(−)-4-benzyl-2-oxazolidinone was treated with hexanoyl chloride to provide acyl oxazolidinone IXc in 96% yield. $^1H$ NMR (300 MHz, $CDCl_3$) δ7.36–7.20 (m, 5H), 4.68 (m, 1H), 4.23–4.14 (m, 2H), 3.30 (dd, J=13.3, 3.3 Hz, 1H), 3.02–2.83 (m, 2H), 2.76 (dd, J=13.3, 9.6 Hz, 1H), 1.70 (m, 2H), 1.43–1.34 (m, 4H), 0.92 (t, J=3.3 Hz, 3H).

d. Acyl oxazolidinone IXd ($R^2$=i-Bu; $R^8$=$CH_2Ph$)

i. 4-Methylvaleryl chloride

4-Methylvaleryl chloride was prepared from commercially available 4-methylvaleric acid in the following way: a cold (0° C.) solution of 4-methylvaleric acid (1.85 mL, 15.0 mmol) in 50 mL anhydrous $CH_2Cl_2$ containing 10 mL of DMF was treated with 1.95 µL oxalyl chloride (22.5 mmol). The mixture was then stirred for 3 h at room temperature, concentrated in vacuo and filtered to affords 1.65 g (100%) of the desired acid chloride as a colorless liquid.

ii. Acyl oxazolidinone IXd ($R^2$=i-Bu; $R^8$=$CH_2Ph$)

By a procedure analogous to that described for preparing acyl oxazolidinone IXb, the lithium anion of (S)-(−)-4-benzyl-2-oxazolidinone was treated with 4-methylvaleryl chloride to provide acyl oxazolidinone IXd in 85% yield. $^1H$ NMR (300 MHz, $CDCl_3$) δ7.37–7.20 (m, 5H), 4.70–4.63

(m, 1H), 4.23–4.15 (m, 2H), 3.30 (dd, J=13.2, 3.2 Hz, 1H), 2.98–2.90 (m, 2H), 2.76 (dd, J=13.3, 9.6 Hz, 1H), 1.68–1.54 (m, 3H), 0.94 (d, J=6.2 Hz, 3H).

e. Acyl oxazolidinone IXe ($R^2$=CH$_2$Ph; $R^8$=CH$_2$Ph)

By a procedure analogous to that described for preparing acyl oxazolidinone IXb, the lithium anion of (S)-(−)-4-benzyl-2-oxazolidinone was treated with hydrocinnamoyl chloride to provide acyl oxazolidinone IXe in 82% yield. $^1$H NMR (300 MHz, CDCl$_3$) δ7.35–7.16 (m, 10H), 4.70–4.63 (m, 1H), 4.21–4.14 (m, 2H), 3.38–3.19 (m, 3H), 3.08–2.98 (m, 2H), 2.75 (dd, J=13.4, 9.5 Hz, 1H).

EXAMPLE 2

Acyl Oxazolidinones (X)

a. Acyloxazolidinone Xb ($R^2$=n-Pr; $R^8$=CH$_2$Ph)

A cold(0° C.) solution of acyl oxazolidinone IXb (5.74 g, 22.0 mmol) in 110 mL anhydrous CH$_2$Cl$_2$ was treated with 2.52 mL TiCl$_4$ (23.1 mmol) resulting in the formation of an abundant precipitate. After 5 min, diisopropylethylamine (4.22 mL, 24.2 mmol) was added slowly and the resulting dark brown solution was stirred at room temperature for 35 min. Benzyl chloromethyl ether (6.0 mL, 44.0 mmol) was rapidly added and the mixture was stirred for 5 h at room temperature. 50 mL CH$_2$Cl$_2$ and 75 mL of 10% aqueous NH$_4$Cl were then added, resulting in the formation of yellow gummy material. After stirring the suspension vigorously for 10 min, the supernatant was transferred in a separatory funnel and the gummy residue was taken up in 100 mL 1:1 10% aqueous NH$_4$Cl/CH$_2$Cl$_2$. The combined organic layers were then washed successively with 1N aqueous HCl, saturated NaHCO$_3$ and brine, dried over MgSO$_4$ and concentrated in vacuo. The crude solid material was recrystallized from EtOAc/hexane affording 6.80 g of desired acyl oxazolidinone Xb as a white solid in 81% yield. $^1$H NMR (300 MHz, CDCl$_3$) δ7.34–7.18 (m, 10H), 4.77–4.69 (m, 1H), 4.55 (s, 2H), 4.32–4.23 (m, 1H), 4.21–4.10 (m, 2H), 3.80 (t, J=9.0 Hz, 1H), 3.65 (dd, J=9.0, 5.0 Hz, 1H), 3.23 (dd, J=13.5, 3.3 Hz, 1H), 2.69 (dd, J=13.5, 9.3 Hz, 1H), 1.74–1.64 (m, 1H), 1.54–1.44 (m, 1H), 1.40–1.28 (m, 2H), 0.91 (t, J=7.3 Hz, 3H). LRMS (FAB) m/e 382 (M+H$^+$)

b. Acyl oxazolidinone Xa ($R^2$=Et; $R^8$=CH$_2$Ph)

By a procedure analogous to that described for preparing acyl oxazolidinone Xb, acyl oxazolidinone Xa was obtained in 80% yield. $^1$H NMR (300 MHz, CDCl$_3$) δ7.36–7.18 (m, 10H), 4.55 (s, 2H), 4.21–4.11 (m, 3H), 3.81 (t, J=9.0 Hz, 1H), 3.66 (dd, J=9.0, 5.0 Hz, 1H), 3.23 (dd, J=13.5, 3.2 Hz, 1H), 2.70 (dd, J=13.5, 9.3 Hz, 1H), 1.78–1.57 (m, 2H), 0.94 (t, J=7.5 Hz, 3H).

c. Acyl oxazolidinone Xc ($R^2$=n-Bu; $R^8$=CH$_2$Ph)

By a procedure analogous to that described for preparing acyl oxazolidinone Xb, acyl oxazolidinone Xc was obtained in 91% yield. $^1$H NMR (300 MHz, CDCl$_3$) δ7.38–7.17(m, 10H), 4.72 (m, 1H), 4.54 (s, 2H), 4.27–4.10 (m, 2H), 3.79 (t, J=8.7 Hz, 1H), 3.65 (dd, J=9.1, 5.0 Hz, 1H), 3.23 (dd, J=13.5, 3.3 Hz, 1H), 2.68 (dd, J=13.5, 9.3 Hz, 1H), 1.75–1.68 (m, 1H), 1.31–1.26 (m, 4H), 0.87 (t, J=6.8 Hz 3H).

d. Acyl oxazolidinone Xd ($R^2$=i-Bu; $R^8$=CH$_2$Ph)

By a procedure analogous to that described for preparing acyl oxazolidinone Xb, acyl oxazolidinone Xd was obtained in 98% yield. $^1$H NMR (300 MHz, CDCl$_3$) δ7.38–7.17 (m, 10H), 4.75–4.67 (m, 1H), 4.57 (d, J=12.0 Hz, 1H), 4.51 (d, J=12.0 Hz, 1H), 4.41–4.36 (m, 1H), 4.20–4.09 (m, 2H), 3.74 (t, J=9.0 Hz, 1H), 3.65 (dd, J=9.0, 5.1 Hz, 1H), 3.23 (dd, J=13.5, 3.2 Hz, 1H), 2.63 (dd, J=13.5, 9.5 Hz, 1H), 1.74–1.52 (m, 2H), 1.35 (dd, J=13.1, 6.1 Hz, 1H), 0.92 (d, J=2.9 Hz, 3H), 0.90 (d, J=2.9 Hz, 3H).

e. Acyl oxazolidinone Xe ($R^2$=CH$_2$Ph; $R^8$=CH$_2$Ph)

By a procedure analogous to that described for preparing acyl oxazolidinone Xb, acyl oxazolidinone Xe was obtained in 84% yield. $^1$H NMR (300 MHz, CDCl$_3$) δ7.38–7.15 (m, 15H), 4.62–4.50 (m, 4H), 4.03 (dd, J=9.0, 2.7 Hz, 1H), 3.93–3.82 (m, 2H), 3.66 (dd, J=9.2, 4.8 Hz, 1H), 3.19 (dd, J=13.5, 3.2 Hz, 1H), 2.98 (dd, J=13.4, 8.2 Hz, 1H), 2.88 (dd, J=13.4, 7.3 Hz, 1H), 2.68 (dd, J=13.5, 9.3 Hz, 1H).

EXAMPLE 3

Carboxylic Acids (XI)

a. Carboxylic acid XIb ($R^2$=n-Pr)

A cold (0° C.) solution of 6.60 g (17.3 mmol) of acyl oxazolidinone Xb in 320 mL THF/H$_2$O was treated successively with 6.95 mL 35% aqueous H$_2$O$_2$ and a solution of lithium hydroxide monohydrate (1.46 g, 34.6 mmol) in 20 mL H$_2$O. The mixture was stirred for 16 h at 0° C. and then treated carefully first with a solution Na$_2$SO$_3$ (10.5 g) in 55 mL H$_2$O and then with a solution of NaHCO$_3$ (4.35 g) in 100 mL H$_2$O. The mixture was stirred for 30 min at room temperature and concentrated in vacuo to remove the THF. The resulting aqueous mixture was then washed with CH$_2$Cl$_2$ (4×75 mL), cooled to 0° C., acidified with 6N aqueous HCl and extracted with CH$_2$Cl$_2$ (1×200 mL and 3×100 mL). The combined organic layers were then dried over MgSO$_4$ and concentrated in vacuo affording 3.47 g (90%) of desired acid XIb as a clear colorless oil. $^1$H NMR (300 MHz, CDCl$_3$) δ7.38–7.26 (m, 5H), 4.55 (s, 2H), 3.67 (m, 1H), 3.57 (dd, J=9.2, 5.2 Hz, 1H), 2.75 (m, 1H), 1.72–1.31 (m, 4H), 0.93 (t, J=7.2 Hz, 3H). LRMS (FAB) m/e 223 (M+H$^+$)

b. Carboxylic acid XIa ($R^2$=Et)

By a procedure analogous to that described for preparing acyl oxazolidinone XIb, acyl oxazolidinone XIa was obtained in 48% yield. $^1$H NMR (300 MHz, CDCl$_3$) δ7.36–7.27 (m, 5H), 4.55 (s, 2H), 3.68 (dd, J=9.2, 7.9 Hz, 1H), 3.59 (dd, J=9.2, 5.4 Hz, 1H), 2.68–2.65 (m, 1H), 1.71–1.62 (m, 2H), 0.97 (t, J=7.5 Hz, 3H).

c. Carboxylic acid XIc ($R^2$=n-Bu)

By a procedure analogous to that described for preparing acyl oxazolidinone XIb, acyl oxazolidinone XIc was obtained in 96% yield. $^1$H NMR (300 MHz, CDCl$_3$) δ7.37–7.28 (m, 5H), 4.55 (s, 2H), 3.67 (dd, J=9.1, 8.1 Hz, 1H), 3.57 (dd, J=9.2, 5.3 Hz, 1H), 2.72 (m, 1H), 1.67–1.51 (m, 2H), 1.36–1.27 (m, 4H), 0.89 (t, J=6.9 Hz, 3H).

d. Carboxylic acid XId ($R^2$=i-Bu)

By a procedure analogous to that described for preparing acyl oxazolidinone XIb, acyl oxazolidinone XId was obtained in 80% yield. $^1$H NMR (300 MHz, CDCl$_3$) δ7.37–7.28 (m, 5H), 4.55 (s, 2H), 3.64 (t, J=9.1 Hz, 1H), 3.54 (dd, J=9.1, 5.1 Hz, 1H), 2.81 (m, 1H), 1.68–1.54 (m, 2H), 1.36–1.27 (m, 1H), 0.92 (d, J=4.9 Hz, 3H), 0.90 (d, J=4.9 Hz, 3H).

e. Carboxylic acid XIe ($R^2$=CH$_2$Ph)

By a procedure analogous to that described for preparing acyl oxazolidinone XIb, acyl oxazolidinone XIe was obtained in 92% yield. $^1$H NMR (300 MHz, CDCl$_3$) δ7.38–7.16 (m, 10H), 4.53 (d, J=12.1 Hz, 1H), 4.50 (d, J=12.1 Hz, 1H), 3.68–3.57 (m, 2H), 3.09–2.85 (m, 3H).

EXAMPLE 4

Diethyl Amides (XII)

a. Diethylamide XIb ($R^2$=n-Pr; $R^5$=$R^6$=Et): A cooled solution (0° C.) of carboxylic acid XIb (3.40 g, 15.3 mmol) in 1:1 MeCN/CH$_2$Cl$_2$ (150 mL), containing diethylamine (2.36 mL, 23.0 mmol) and 2-(1H-benzotriazol-1-yl)-1,1,3,3- tetramethyluronium tetrafluoroborate (TBTU, 5.89 g, 18.4 mmol), was treated with diisopropylethylamine (6.7 mL, 38.2 mmol) over 1.5 h (syringe pump). The mixture was then concentrated in vacuo and partitioned between ether (200 mL) and $H_2O$ (100 mL). The aqueous layer was extracted with more ether (2×100 mL) and the combined organic layers were washed with aqueous 1N HCl (3×50 mL), saturated aqueous $NaHCO_3$ and brine, dried over $MgSO_4$ and concentrated in vacuo. Chromatographic purification (230–400 mesh $SiO_2$, elution with 1:3 AcOEt/hexane) afforded 4.24 g (97%) of diethyl amide XIIb as a clear colorless oil. $^1H$ NMR (300 MHz, $CDCl_3$) δ7.35–7.23 (m, 5H), 4.52 (d, J=12.0 Hz, 1H), 4.44 (d, J=12.0 Hz, 1H), 3.67 (t, J=8.6 Hz, 1H), 3.51 (dd, J=8.7, 5.5 Hz, 1H), 3.46–3.27 (m, 4H), 2.96 (m, 1H), 1.67–1.57 (m, 1H), 1.48–1.22 (m, 4H), 1.20–1.10 (m, 6H), 0.90 (t, J=7.2 Hz, 3H). LRMS (FAB) m/e 278 (M+H$^+$)

b. Diethylamide XIIa ($R^2$=Et; $R^5$=$R^6$=Et)

By a procedure analogous to that described for preparing diethylamide XIIb, diethylamide XIIa was obtained in 73% yield. $^1H$ NMR (300 MHz, $CDCl_3$) δ7.33–7.26 (m, 5H), 4.52 (d, J=12.0 Hz, 1H), 4.44 (d, J=12.0 Hz, 1H), 3.68 (t, J=8.6 Hz, 1H), 3.53–3.33 (m, 5H), 2.90 (m, 1H), 1.75–1.50 (m, 2H), 1.18 (t, J=7.1 Hz, 3H), 1.13 (t, J=7.1 Hz, 3H), 0.89 (t, J=7.4 Hz, 3H).

c. Diethylamide XIIc ($R^2$=n-Bu; $R^5$=$R^6$=Et)

By a procedure analogous to that described for preparing diethylamide XIIb, diethylamide XIIc was obtained in 94% yield. $^1H$ NMR (300 MHz, $CDCl_3$) δ7.35–7.25 (m, 5H), 4.51 (d, J=12.0 Hz, 1H), 4.44 (d, J=12.0 Hz, 1H), 3.67 (t, J=8.6 Hz, 1H), 3.51 (dd, J=8.8, 5.5 Hz, 1H), 3.46–3.29 (m, 1H), 2.94 (m, 1H), 1.66–1.62 (m, 2H), 1.33–1.10 (m, 9H), 0.85 (t, J=7.0 Hz, 3H).

d. Diethylamide XIId ($R^2$=i-Bu; $R^5$=$R^6$=Et)

By a procedure analogous to that described for preparing diethylamide XIIb, diethylamide XIId was obtained in 95% yield. $^1H$ NMR (300 MHz, $CDCl_3$) δ7.35–7.23 (m, 5H), 4.51 (d, J=12.0 Hz, 1H), 4.44 (d, J=12.0 Hz, 1H), 3.65 (t, J=8.7 Hz, 1H), 3.54–3.28 (m, 5H), 3.03 (m, 1H), 1.63–1.49 (m, 2H), 1.33–1.24 (m, 1H), 1.18 (t, J=7.1 Hz, 3H), 1.12 (t, J=7.1 Hz, 3H), 0.90 (t, J=6.4 Hz, 3H).

e. Diethylamide XIIe ($R^2$=$CH_2Ph$; $R^5$=$R^6$=Et)

By a procedure analogous to that described for preparing diethylamide XIIb, diethylamide XIIe was obtained in 89% yield. $^1H$ NMR (300 MHz, $CDCl_3$) δ7.35–7.16 (m, 10H), 4.53 (d, J=12.1 Hz, 1H), 4.47 (d, J=12.1 Hz, 1H), 3.77 (t, J=8.5 Hz, 1H), 3.59 (dd, J=8.8, 5.7 Hz, 1H), 3.40 (m, 1H), 3.22–2.89 (m, 5H), 2.79 (dd, J=13.0, 5.1 Hz, 3H), 1.01 (t, J=7.1 Hz, 3H), 0.85 (t, J=7.2 Hz, 3H).

EXAMPLE 5

Alcohols (XIII)

a. Alcohol XIIIb ($R^2$=n-Pr; $R^5$=$R^6$=Et)

To a solution of diethylamide XIIb (4.08 g, 14.7 mmol) in 140 mL MeOH was added 20% Pd(OH)$_2$/C (400 mg) and the suspension was hydrogenated at atmospheric pressure and room temperature for 15 h. Filtration of the catalyst and concentrating the filtrate in vacuo afforded 2.84 g (100%) of the desired primary alcohol XIIIb. $^1H$ NMR (300 MHz, $CDCl_3$) δ3.74 (br. d, J=4.2 Hz, 1H), 3.61–3.15 (m, 5H), 2.71 (m, 1H), 1.69–1.24 (m, 4H), 1.20 (t, J=7.1 Hz, 3H), 1.12 (t, J=7.1 Hz, 3H), 0.92 (t, J=7.2 Hz, 3H). LRMS (FAB) m/e 188 (M+H$^+$).

b. Alcohol XIIIa ($R^2$=Et; $R^5$=$R^6$=Et)

By a procedure analogous to that described for preparing alcohol XIIIb, alcohol XIIIa was obtained in 100% yield. $^1H$ NMR (300 MHz, $CDCl_3$) δ3.76 (m, 2H), 3.58–3.19 (m, 4H), 2.64 (m, 1H), 1.71–1.65 (m, 2H), 1.21 (t, J=7.1 Hz, 3H), 1.13 (t, J=7.1 Hz, 3H), 0.96 (t, J=7.4 Hz, 3H).

c. Alcohol XIIIc ($R^2$=n-Bu; $R^5$=$R^6$=Et)

By a procedure analogous to that described for preparing alcohol XIIIb, alcohol XIIIc was obtained in 100% yield. $^1H$ NMR (300 MHz, $CDCl_3$) δ3.76 (d, J=4.5 Hz, 2H), 3.58–3.19 (m, 4H), 2.72–2.65 (m, 2H), 1.68–1.55 (m, 2H), 1.40–1.24 (m, 4H), 1.20 (t, J=7.1 Hz, 3H), 1.12 (t, J=7.1 Hz, 3H), 0.90 (t, J=6.9 Hz, 3H).

d. Alcohol XIIId ($R^2$=i-Bu; $R^5$=$R^6$=Et)

By a procedure analogous to that described for preparing alcohol XIIIb, alcohol XIIId was obtained in 100% yield. $^1H$ NMR (300 MHz, $CDCl_3$) δ3.78–3.68 (m, 2H), 3.57–3.15 (m, 4H), 2.81–2.73 (m, 1H), 1.70–1.60 (m, 2H), 1.40–1.28 (m, 1H), 1.21 (t, J=7.1 Hz, 3), 1.12 (t, J=7.1 Hz, 3H), 0.92 (m, 6H).

e. Alcohol XIIIe ($R^2$=$CH_2Ph$; $R^5$=$R^6$=Et)

By a procedure analogous to that described for preparing alcohol XIIIb, alcohol XIIIe was obtained in 100% yield. $^1H$ NMR (300 MHz, $CDCl_3$) δ7.29–7.16 (m, 5H), 3.81–3.71 (m, 2H), 3.61–3.50 (m, 1H), 3.15–2.87 (m, 6H), 1.05 (t, J=7.1 Hz, 3H), 0.98 (t, J=7.1 Hz, 4H), 3H).

EXAMPLE 6

Aldehydes (XIV)

a. Aldehyde XIVb ($R^2$=n-Pr; $R^5$=$R^6$=Et)

To a solution of alcohol XIIIb (2.34 g, 12.7 mmol) in wet $CH_2Cl_2$ (125 mL, prepared by stirring $CH_2Cl_2$ with water and separating the organic layer) was added Dess-Martin periodinane (8.06 g, 19.0 mmol). The mixture was stirred at room temperature for 40 min and was then poured into a mixture of 5% aqueous $Na_2S_2O_3$ (250 mL) containing 5.2 g $NaHCO_3$, and ether (200 mL). The biphasic mixture was stirred vigorously for 5 min and the aqueous layer was extracted with 15% $CH_2Cl_2/Et_2O$ (2×100 mL). The combined organic layers were then washed with $H_2O$ (3×75 mL) and brine, dried over $MgSO_4$, filtered and concentrated in vacuo to afford 2.06 g (88%) of desired aldehyde XIVb, a clear colorless oil. $^1H$ NMR (300 MHz, $CDCl_3$) δ9.60 (d, J=3.5 Hz, 1H), 3.49–3.30 (m, 5H), 1.96–1.85 (m, 2H), 1.39–1.31 (m, 2H), 1.19 (t, J=7.1 Hz, 3H), 1.13 (t, J=7.1 Hz, 3H), 0.95 (t, J=7.3 Hz, 3H).

b. Aldehyde XIVb ($R^2$=n-Pr; $R^5$=$R^6$=Et)

To a solution of crude XIIIb (1.25 g, 6.68 mmol) in a mixture of toluene (20 mL), ethyl acetate (20 mL), and water (3 mL) was added 2,2,6,6-tetramethyl-1-piperidinyloxy (TEMPO), free radical (9 mg). The mixture was cooled to 0° C. and a sodium hypochlorite solution, prepared by adding 4.3 mL of aqueous sodium hypochlorite (10–13% available chlorine) to 1.6 g of $NaHCO_3$ in 20 mL of water, was added by portions over a period of 30 min. Sodium bromide (660 mg) was added and the solution turned pale orange. Within a few minutes the color of the reaction mixture returned to off-white. Additional sodium hypochlorite (4.7 mL) was added in several portions to drive the reaction to completion. The aqueous layer was separated and extracted with toluene (20 mL) and ethyl acetate (2×20 mL). The combined organic extract was washed with a solution of KI (70 mg) in 10% aqueous $KHSO_4$. The organic layer was then washed with 5% $Na_2S_2O_3$ and pH 7 phosphate buffer, dried ($Na_2SO_4$), and concentrated to give XIVb as a pale yellow oil (1.1 g). Spectral data for this compound matched that for the product from Example 6a above.

c. Aldehyde XIVa ($R^2$=Et; $R^5$=$R^6$=Et)

By a procedure analogous to that described for preparing alcohol XIVb, aldehyde XIVa was obtained in 80% yield. $^1H$ NMR (300 MHz, $CDCl_3$) δ9.61 (d, J=3.6 Hz, 1H), 3.48–3.29 (m, 5H), 2.02–1.90 (m, 2H), 1.19 (t, J=7.1 Hz, 3H), 1.14 (t, J=7.1 Hz, 3H), 0.96 (t, J=7.4 Hz, 3H).

d. Aldehyde XIVc ($R^2$=n-Bu; $R^5$=$R^6$=Et)

By a procedure analogous to that described for preparing alcohol XIVb, aldehyde XIVc was obtained in 98% yield. $^1$H NMR (300 MHz, CDCl$_3$) δ9.59 (d, J=3.6 Hz, 1H), 3.48–3.29 (m, 5H), 1.97–1.87 (m, 2H), 1.39–1.22 (m, 4H), 1.18 (t, J=7.2 Hz, 3H), 1.13 (t, J=7.2 Hz, 3H), 0.90 (t, J=7.0 Hz, 3H).

e. Aldehyde XIVd ($R^2$=i-Bu; $R^5$=$R^6$=Et)

By a procedure analogous to that described for preparing alcohol XIVb, aldehyde XIVd was obtained in 96% yield. $^1$H NMR (300 MHz, CDCl$_3$) δ9.57 (d, J=3.7 Hz, 1H), 3.51–3.27 (m, 5H), 1.83 (t, J=7.1 Hz, 3H), 1.66–1.55 (m, 1H), 1.20 (t, J=7.1 Hz, 3H), 1.13 (t, J=7.1 Hz, 3H), 0.93 (d, J=6.6 Hz, 6H).

f. Aldehyde XIVe ($R^2$=CH$_2$Ph; $R^5$=$R^6$=Et)

By a procedure analogous to that described for preparing alcohol XIVb, aldehyde XIVe was obtained in 97% yield. $^1$H NMR (300 MHz, CDCl$_3$) δ9.69 (d, J=2.9 Hz, 1H), 7.29–7.16 (m, 5H), 3.65 (m, 1H), 3.53–3.42 (m, 1H), 3.30 (dd, J=13.5, 9.3 Hz, 1H), 3.23–3.13 (m, 2H), 3.06–2.91 (m, 2H), 1.04 (t, J=7.1 Hz, 3H), 0.93 (t, J=7.1 Hz, 3H).

The preparation of clasto-lactacystin β-lactone and analogs thereof according to the synthetic scheme outlined in Scheme 1 as exemplified in Examples 7–9.

EXAMPLE 7

Aldol Adducts (II)

a. Aldol adduct IIb ($R^2$=n-Pr; $R^1$=i-Pr; $R^3$=Me; $R^4$=Ph; $R^5$=$R^6$=Et)

To a cold (−78° C.) solution of trans-oxazoline Ia ($R^1$=i-Pr; $R^4$=Ph) in ether (35 mL) was added lithium bis(trimethylsilyl)amide (2.17 of a 1 M solution in hexane, 2.17 mmol). After 30 min, the orange solution was treated dropwise with a 1M solution of dimethylaluminum chloride in hexane (4.55 mL, 4.55 mmol) and the mixture was stirred for another 60 min before being cooled down to −85° C. (liquid N$_2$ was added to the dry ice/acetone bath). A solution of aldehyde XIVb (420 mg, 2.27 mmol) in ether (4 mL) was then added over 10 min along the side of the flask. The mixture was then allowed to warm up to −40° C. over 2.5 h and then quenched by adding 35 mL of saturated aqueous NH$_4$Cl and 25 mL AcOEt. Enough 2 N HCl was then added until 2 clear phases were obtained (ca. 15 mL added). The aqueous layer was extracted with AcOEt (2×20 mL) and the combined organic layers were washed successively with 0.5 N aqueous HCl (20 mL), H$_2$O (20 mL), 0.5 M aqueous NaHSO$_3$ (2×15 mL), saturated aqueous NaHCO$_3$ and finally with brine, then dried over Na$_2$SO$_4$ and concentrated in vacuo affording 879 mg (>100%) of crude Aldol product IIb which was pure enough to be used directly in the subsequent step. $^1$H NMR (300 MHz, CDCl$_3$) δ8.02–7.97 and 7.53–7.39 (m, 5H), 6.58 (d, J=9.9 Hz, 1H), 4.82 (d, J=2.4 Hz, 1H), 3.73 (s, 3H), 3.69–3.61 (m, 2H), 3.49–3.39 (m, 2H), 3.24–3.16 (m, 1H), 3.05 (m, 1H), 2.89 (m, 1H), 2.28–2.23 (m, 1H), 1.98–1.91 (m, 1H), 1.37–1.20 (m, 6H), 1.19–1.06 (m, 6H), 0.87 (t, J=7.1 Hz, 3H), 0.70 (d, J=6.7 Hz, 3H).

Aldol product IIb was also obtained in 100% yield by a procedure analogous to that described above but using cis-oxazoline Ib (see below) instead of trans-oxazoline Ia.

b. Aldol adduct IIb ($R^2$=n-Pr; $R^1$=i-Pr; $R^3$=Me; $R^4$=Ph; $R^5$=$R^6$=Et)

To a cold (−78° C.) solution of trans-oxazoline Ia ($R^1$=i-Pr; $R^4$=Ph) (20.74 g) in THF (280 mL) was added lithium bis(trimethylsilyl)amide (92.4 mL of a 1 M solution in hexane) over 75 min. After 30 min, the orange solution was treated dropwise with a 1M solution of dimethylaluminum chloride in hexane (202 mL) and the mixture was stirred for another 40 min before being cooled down to −85° C. (liquid N$_2$ was added to the dry ice/acetone bath). A solution of aldehyde XIVb (19.43 g) in THF (50 mL) was then added over 45 min. The mixture was then allowed to warm to −50° C. over 40 min and then to −20° C. over 25 min. The yellow reaction mixture was again cooled to −78° C. and then quenched by cautious addition of 40 mL of saturated aqueous NH$_4$Cl. The reaction mixture was poured slowly into 460 mL of saturated aqueous NH$_4$Cl. AcOEt (500 mL) was added, and with good stirring the reaction mixture was acidifed with 6 N HCl to produce two clear phases. The aqueous layer was extracted with AcOEt (2×200 mL), and the combined organic layers were washed successively with H$_2$O (2×200 mL), saturated aqueous NaHCO$_3$ (2×200 mL), and brine (2×300 mL). The organic extract was dried over Na$_2$SO$_4$ and MgSO$_4$ and concentrated in vacuo to afford 41.55 g of crude Aldol product IIb which was pure enough to be used directly in the subsequent step. Spectral data for this compound matched that for the product from Example 7a above.

c. Aldol adduct IIa ($R^2$=Et; $R^1$=i-Pr; $R^3$=Me; $R^4$=Ph; $R^5$=$R^6$=Et)

By a procedure analogous to that described for preparing Aldol adduct IIb, the lithium anion of trans-oxazoline Ia ($R^1$=i-Pr; $R^4$=Ph) was treated successively with dimethylaluminum chloride and aldehyde XIVa to provide Aldol adduct IIa in 95% yield. $^1$H NMR (300 MHz, CDCl$_3$) δ8.00–7.97 and 7.51–7.39 (m, 5H), 6.50 (d, J=9.9 Hz, 1H), 4.80 (d, J=2.4 Hz, 1H), 3.81–3.64 (m, 2H), 3.74 (s, 3H), 3.45 (m, 2H), 3.19 (m, 2H), 2.93–2.84 (m, 2H), 2.24 (m, 1H), 1.89 (m, 1H), 1.73–1.64 (m, 4H), 1.29 (t, J=7.2 Hz, 3H), 1.12 (d, J=6.9 Hz, 3H), 1.07 (d, J=7.2 Hz, 3H), 0.70 (d, J=6.7 Hz, 3H).

d. Aldol adduct IIc ($R^2$=n-Bu; $R^1$=i-Pr; $R^3$=Me; $R^4$=Ph; $R^5$=$R^6$=Et)

By a procedure analogous to that described for preparing Aldol adduct IIb, the lithium anion of trans-oxazoline Ia ($R^1$=i-Pr; $R^4$=Ph) was treated successively with dimethylaluminum chloride and aldehyde XIVc to provide Aldol adduct IIc in 100% yield. $^1$H NMR(300 MHz, CDCl$_3$) δ8.02–7.98 and 7.53–7.33 (m, 5H), 6.57 (d, J=10.0 Hz, 1H), 4.81 (d, J=2.3 Hz, 1H), 3.73 (s, 3H), 3.68–3.60 (m, 2H), 3.49–3.17 (m, 2H), 3.00 (m, 1H), 2.90 (m, 1H), 1.98–1.87 (m, 2H), 1.38–0.83 (m, 16H), 0.70 (d, J=6.7 Hz, 3H).

e. Aldol adduct IId ($R^2$=i-Bu; $R^1$=i-Pr; $R^3$=Me; $R^4$=Ph; $R^5$=$R^6$=Et)

By a procedure analogous to that described for preparing Aldol adduct IIb, the lithium anion of trans-oxazoline Ia ($R^1$=i-Pr; $R^4$=Ph) was treated successively with dimethylaluminum chloride and aldehyde XIVd to provide Aldol adduct IId in 100% yield. $^1$H NMR (300 MHz, CDCl$_3$) δ8.01–7.80 and 7.55–7.20 (m, 5H), 4.87 (d, J=2.3 Hz, 1H), 3.73 (s, 3H), 3.69–3.58 (m, 2H), 3.51–3.32 (m, 2H), 2.98–2.87 (m, 1H), 2.33–2.24 (m, 1H), 2.12–2.02 (m, 1H), 1.83 (t, J=7.1 Hz, 1H), 1.35 (t, J=7.1 Hz, 3H), 1.25–1.05 (m, 5H), 0.93 (d, J=6.6 Hz, 3H), 0.89 (d, J=6.5 Hz, 3H), 0.80 (d, J=6.5 Hz, 3H), 0.69 (d, J=6.7 Hz, 3H).

f. Aldol adduct IIe ($R^2$=CH$_2$Ph; $R^1$=i-Pr; $R^3$=Me; $R^4$=Ph; $R^5$=$R^6$=Et)

By a procedure analogous to that described for preparing Aldol adduct IIb, the lithium anion of trans-oxazoline Ia ($R^1$=i-Pr; $R^4$=Ph) was treated successively with dimethylaluminum chloride and aldehyde XIVe to provide Aldol adduct IIe in 100% yield. $^1$H NMR (300 MHz, CDCl$_3$) δ8.01–7.93 and 7.54–7.10 (m, 10H), 4.71 (d, J=2.5 Hz, 1H), 3.73 (s, 3H), 3.68–3.58 (m, 2H), 3.48–2.79 (m, 6H), 2.17 (m, 1H), 1.12–0.91 (m, 9H), 0.68 (d, J=6.7 Hz, 3H).

EXAMPLE 8

γ-Lactams (IV)

a. γ-Lactam IVb ($R^2$=n-Pr; $R^1$=i-Pr; $R^3$=Me)

A solution of Aldol adduct IIb (4.72 g, 10.9 mmol) in 100 mL 1:9 AcOH/MeOH, to which was added 4.8 g 20% Pd(OH)$_2$/C, was vigorously shaken under 55 p.s.i. H$_2$ for 60 h. The mixture was brought down to atmospheric temperature before being filtered and concentrated in vacuo. The solid obtained was purified by flash chromatography (SiO$_2$, elution with 1% AcOH in 1:1 AcOEt/hexane) affording 2.23 g (75%) of desired γ-lactam IVb as a white solid. $^1$H NMR (300 MHz, CDCl$_3$) δ7.89 (br. s, 1H), 4.77 (br. d, J=11.5 Hz, 1H), 4.47 (dd, J=11.5, 5.6 Hz, 1H), 4.08 (dd, J=9.4, 5.0 Hz, 1H), 3.83 (s, 3H), 2.93 (m, 1H), 1.78–1.39 (m, 6H), 1.02–0.88 (m, 9H).

b. γ-Lactam IVa ($R^2$=Et; $R^1$=i-Pr; $R^3$=Me)

By a procedure analogous to that described for preparing γ-lactam IVb, Aldol adduct IIa was hydrogenated at 55 p.s.i. for 48 h to provide γ-lactam IVa in 72% yield. $^1$H NMR (300 MHz, CDCl$_3$) δ7.79 (br. s, 1H), 4.62 (br. d, J=11.2 Hz, 1H), 4.51 (dd, J=11.2, 5.4 Hz, 1H), 3.83 (s, 3H), 2.85 (m, 1H), 1.77–1.64 (m, 3H), 1.01 (t, J=7.4 Hz, 3H), 0.98 (d, J=6.9 Hz, 3H), 0.95 (d, J=6.9 Hz, 3H).

c. γ-Lactam IVc ($R^2$=n-Bu; $R^1$=i-Pr; $R^3$=Me)

A solution of Aldol adduct IIc (361 mg, 0.80 mmol) in 6 mL 1:9 AcOH/MeOH, to which was added 250 mg 20% Pd(OH)$_2$/C, was vigorously shaken under 50 p.s.i. H$_2$ for 24 h. More catalyst (100 mg) was then added and the mixture was again shaken at 50 p.s.i. for another 24 h after which time it brought down to atmospheric temperature before being filtered. The filtrate was then heated to reflux for 30 min, cooled to room temperature and concentrated in vacuo. The solid obtained was co-evaporated once with toluene and purified by flash chromatography (SiO$_2$, elution with 4% MeOH/CHCl$_3$) affording 140 mg (61%) of desired γ-lactam IVc as a white solid. $^1$H NMR (300 MHz, CDCl$_3$) δ8.02 (br. s, 1H), 4.93 (br. d, J=11.3 Hz, 1H), 4.46 (dd, J=11.3, 5.5 Hz, 1H), 4.15–4.08 (m, 1H), 3.83 (s, 3H), 2.94–2.87 (m, 1H), 1.80–1.34 (m, 6H), 0.94 (d, J=6.9 Hz, 3H), 0.89 (t, J=7.2 Hz, 3H).

d. γ-Lactam IVd ($R^2$=i-Bu; $R^1$=i-Pr; $R^3$=Me)

By a procedure analogous to that described for preparing γ-lactam IVc, Aldol adduct IId was hydrogenated at 50 p.s.i. for 40 h and heated to reflux for 30 min providing γ-lactam IVd in 61% yield. $^1$H NMR (300 MHz, CDCl$_3$) δ7.92 (br. s, 1H), 4.81 (br. d, J=11.5 Hz, 1H), 4.46 (m, 1H), 4.09 (m, 1H), 3.83 (s, 3H), 3.04–2.98 (m, 1H), 1.78–1.73 (m, 2H), 1.66–1.47 (m, 3H), 1.00–0.90 (m, 12H).

e. γ-Lactam IVe ($R^2$=CH$_2$Ph; $R^1$=i-Pr; $R^3$=Me)

By a procedure analogous to that described for preparing γ-lactam IVc, Aldol adduct IIe was hydrogenated at 50 p.s.i. for 24 h and heated to reflux for 30 min providing γ-lactam IVe in 71% yield. $^1$H NMR (300 MHz, CDCl$_3$) δ8.01 (br. s, 1H), 7.35–7.15 (m, 5H), 5.02 (br. d, J=11.7 Hz, 1H), 4.40–4.34 (m, 1H), 4.06–4.01 (m, 1H), 3.84 (s, 3H), 3.34–3.27 (m, 1H), 3.10–3.04 (m, 2H), 1.84–1.72 (m, 1H), 0.98 (d, J=6.7 Hz, 3H), 0.93 (d, J=6.9 Hz, 3H).

EXAMPLE 9

β-Lactones (VII)

a. β-Lactone VIIb ($R^2$=n-Pr; $R^1$=i-Pr)

To a cold (0° C.) solution of γ-lactam IVb (2.20 g, 8.06 mmol) in EtOH (100 mL) was added 0.1N aqueous NaOH (100 mL, 10.0 mmol). The mixture was stirred at room temperature for 15 h after which time H$_2$O (50 mL) and AcOEt (100 mL) were added. The aqueous layer was then washed with AcOEt (2×50 mL), acidified with 6N aqueous HCl and concentrated in vacuo to a volume of ca 60 mL. This solution was then frozen and lyophilized. The obtained solid was suspended in THF, filtered to get rid of sodium chloride and concentrated in vacuo affording 2.05 g (98%) of the desired dihydroxyacid as white solid. $^1$H NMR (300 MHz, CD$_3$OD) δ4.42 (d, J=5.8 Hz, 1H), 3.90 (d, J=6.5 Hz, 1H), 2.84 (m, 1H), 1.70–1.24 (m, 6H), 0.95–0.84 (m, 9H).

To a solution of the dihydroxyacid (1.90 g, 7.33 mmol) in anhydrous THF (36 mL) was added a solution of 2-(1H-benzotriazol-1-yl)-1,1,3,3-tetramethyluronium tetrafluoroborate (TBTU, 2.59, 8.06 mmol) in anhydrous MeCN (36 mL) followed by triethylamine (0.72 mL, 22.0 mmol). After stirring for 70 min at room temperature, some toluene was added and the mixture was concentrated in vacuo and co-evaporated 2 more times with toluene. Purification by flash chromatography (SiO$_2$, elution with 2:3 AcOEt/hexane) afforded 1.44 g (81%) of desired β-lactone VIIb as a white solid. $^1$H NMR (300 MHz, CDCl$_3$) δ6.07 (br. s, 1H), 5.26 (d, J=6.1 Hz, 1H), 3.97 (dd, J=6.4, 4.4 Hz, 1H), 2.70–2.63 (m, 1H), 2.03 (d, J=6.4 Hz, 3H), 1.93–1.44 (m, 5H), 1.07 (d, J=7.0 Hz, 3H), 0.99 (d, J=7.3 Hz, 3H), 0.91 (d, J=6.7 Hz, 3H). LRMS (FAB) m/e 242 (M+H$^+$).

b. β-Lactone VIIa ($R^2$=Et; $R^1$=i-Pr)

Hydrolysis of IVa, as described for IVb above, afforded the corresponding dihydroxyacid in 100% yield. $^1$H NMR (300 MHz, CD$_3$OD) δ4.45 (d, J=5.8 Hz, 1H), 3.90 (d, J=6.4 Hz, 1H), 2.74 (m, 1H), 1.71–1.53 (m, 3H), 0.94 (t, J=7.4 Hz, 3H), 0.92 (d, J=6.8 Hz, 3H), 0.88 (d, J=6.8 Hz, 3H).

By a procedure analogous to that described for preparing β-lactone VIIb, β-lactone VIIa was obtained in 79% yield. $^1$H NMR (300 MHz, CDCl$_3$) δ6.17 (br. s, 1H), 5.30 (d, J=6.0 Hz, 1H), 3.98 (dd, J=6.4, 4.4 Hz, 1H), 2.60 (m, 1H), 2.08 (d, J=6.4 Hz, 3H), 1.97 (m, 2H), 1.75 (m, 1H), 1.12 (t, J=7.5 Hz, 3H), 1.07 (d, J=6.8 Hz, 3H), 0.92 (d, J=6.8 Hz, 3H).

c. β-Lactone VIIc ($R^2$=n-Bu; $R^1$=i-Pr)

Hydrolysis of IVc, as described for IVb above, afforded the corresponding dihydroxyacid in 100% yield. $^1$H NMR (300 MHz, CD$_3$OD) δ4.42 (d, J=5.8 Hz, 1H), 3.90 (d, J=6.4 Hz, 1H), 2.86–2.79 (m, 1H), 1.70–1.24 (m, 8H), 0.97–0.86 (m, 9H).

By a procedure analogous to that described for preparing β-lactone VIIb, β-lactone VIIc was obtained in 40% yield. $^1$H NMR (300 MHz, CDCl$_3$) δ6.14 (br. s, 1H), 5.27 (d, J=6.1 Hz, 1H), 3.97 (d, J=4.4 Hz, 1H), 2.68–2.61 (m, 1H), 1.94–1.86 (m, 2H), 1.72–1.36 (m, 7H), 1.07 (d, J=7.0 Hz, 3H), 0.93 (t, J=7.1 Hz, 3H), 0.91 (d, J=6.8 Hz, 3H). LRMS (FAB) m/e 256 (M+H$^+$)

d. β-Lactone VIId ($R^2$=i-Bu; $R^1$=i-Pr)

Hydrolysis of IVd, as described for IVb above, afforded the corresponding dihydroxyacid in 100% yield. $^1$H NMR (300 MHz, CD$_3$OD) δ4.50 (d, J=5.8 Hz, 1H), 4.00 (d, J=6.5 Hz, 1H), 3.09–3.02 (m, 1H), 1.90–1.61 (m, 3H), 1.49–1.40 (m, 2H), 1.02 (d, J=6.7 Hz, 3H), 0.98 (d, J=6.5 Hz, 3H), 0.97 (d, J=6.7 Hz, 3H).

By a procedure analogous to that described for preparing β-lactone VIIb, β-lactone VIId was obtained in 62% yield. $^1$H NMR (300 MHz, CDCl$_3$) δ6.16 (br. s, 1H), 5.25 (d, J=6.1 Hz, 1H), 3.97 (d, J=4.4 Hz, 1H), 2.71 (dd, J=15.1, 6.2 Hz, 1H), 1.95–1.66 (m, 5H), 1.08 (d, J=6.9 Hz, 3H), 0.99 (d, J=6.3 Hz, 3H), 0.98 (d, J=6.3 Hz, 3H), 0.92 (d, J=6.7 Hz, 3H). LRMS (FAB) m/e 256 (M+H$^+$).

e. β-Lactone VIIe ($R^2$=CH$_2$Ph; $R^1$=i-Pr)

Hydrolysis of IVe, as described for IVb above, afforded the corresponding dihydroxyacid in 88% yield. $^1$H NMR (300 MHz, CD$_3$OD) δ7.25–7.04 (m, 5H), 4.29 (d, J=5.7 Hz, 1H), 3.83 (d, J=6.4 Hz, 1H), 3.01–2.82 (m, 3H), 1.65 (m, 1H), 0.90 (d, J=6.6 Hz, 3H), 0.86 (d, J=6.8 Hz, 3H).

By a procedure analogous to that described for preparing β-lactone VIIb, β-lactone VIIe was obtained in 77% yield. $^1$H NMR (300 MHz, CDCl$_3$) δ7.36–7.20 (m, 5H), 6.57 (br. s, 1H), 5.08 (d, J=5.4 Hz, 1H), 3.94 (d, J=4.5 Hz, 1H), 3.25 (d, J=10.1 Hz, 1H), 3.01–2.89 (m, 2H), 1.92–1.81 (m, 1H), 1.05 (d, J=6.9 Hz, 3H), 0.86 (d, J=6.7 Hz, 3H). LRMS (FAB) m/e 290 (M+H$^+$).

The preparation of cis-oxazolines and trans-oxazolines according to the synthetic schemes illustrated in Schemes 3 and 4 as illustrated by Examples 10 and 11.

EXAMPLE 10 cis-Oxazoline (Ia)

a. Ethyl 3-(isopropyl)propenoate (XV; R$^1$=i-Pr; R$^3$=Me)

To a stirred solution of carbomethoxymethylene triphenylphosphorane (56.04 g, 167.6 mmol) in dry CH$_2$Cl$_2$ (168 mL) at 0° C. was added dropwise isobutyraldehyde (17.4 mL, 191.6 mmol). After 5 min, the reaction mixture was warmed to room temperature and stirred for 24 h. The solvent was removed in vacuo and pentane was added to the white oily solid to precipitate triphenylphosphine oxide. The solid was filtered off and the filtrate concentrated in vacuo. The procedure was repeated one more time and the crude olefin (20.00 g, 93%) was obtained as a yellow oil that was sufficiently pure for the next step. $^1$H NMR (300 MHz, CDCl$_3$) δ6.95 (dd, J=15.7, 6.6 Hz, 1H), 5.77 (dd, J=15.7, 1.5 Hz), 3.72 (s, 3H), 2.44 (m, 1H), 1.06 (d, J=6.7 Hz, 6H).

b. (2S,3R)-Methyl 2,3-dihydroxy-3-[isopropyl]propionate (XVIa; R$^1$=i-Pr; R$^3$=Me)

A mixture of AD-mix-β (100.00 g,), methanesulfonamide (6.78 g, 71.3 mmol) and tert-butanol-water (1:1, 720 mL) was stirred vigorously at room temperature for 5 min. The reaction mixture was then cooled to 0° C. and α,β-unsaturated ester XV (R$^1$=i-Pr; R$^3$=Me) (9.14 g, 71.3 mmol) was added dropwise via a Pasteur pipette. After stirring at 0° C. for 96 h, Na$_2$SO$_3$ (3.0 g) was added, and stirring continued at room temperature for 1 h. The mixture was diluted with ethyl acetate (200 mL) and transferred to a separatory funnel. The organic layer was removed and the aqueous phase extracted with ethyl acetate (2×100 mL). The combined organic layers were dried (Na$_2$SO$_4$), filtered, and concentrated in vacuo. The yellow oil obtained was passed through a silica gel pad using 1:1 hexane/ethyl acetate affording diol XVIa (R$^1$=i-Pr; R$^3$=Me) (11.48 g, 94%) as a yellow solid. $^1$H NMR (300 MHz, CDCl$_3$) δ4.28 (dd, J=5.6, 1.8 Hz, 1H), 3.80 (s, 3H), 3.48 (m, 1H), 3.28 (m, 1H), 2.33 (d, J=9.3 Hz, 1H), 1.87 (m, 1H), 1.02 (d, J=6.7 Hz, 3H), 0.95 (d, J=6.7 Hz, 3H).

c. (2R,3R)-Methyl 2-bromo-3-dihydroxy-3-(isopropyl)propionate (XVIIa; R$^1$=i-Pr; R$^3$=Me)

(2S,3R)-Methyl 2,3-dihydroxy-3-[isopropyl]propionate XVIa (R$^1$=i-Pr; R$^3$=Me) (1.0 g, 6.17 mmol) and trimethylorthobenzoate (1.02 mL, 80.1 mmol) were dissolved in CH$_2$Cl$_2$ (20 mL) and treated with BF$_3$.OEt$_2$ (40.0 μL, 0.32 mmol). After stirring for 75 min, the mixture was concentrated under full vacuum (0.05 mm Hg) for 35 min. The mixture was redissolved in CH$_2$Cl$_2$ (20.0 mL), cooled to 0° C. and treated sequentially with Et$_3$N (43.0 μL, 0.31 mmol) and acetyl bromide (0.48 mL, 6.49 mmol). After stirring for 4 h at 0° C., the reaction mixture was treated with saturated NaHCO$_3$ solution (12 mL) and allowed to warm up to room temperature. The layers were separated and the aqueous layer was extracted with CH$_2$Cl$_2$ (2×20 mL). The combined organic layers were dried (Na$_2$SO$_4$), filtered and concentrated in vacuo affording the crude α-bromo β-benzoate XVIIa (R$^1$=i-Pr; R$^3$=Me) (1.36 g, 85%) as a clear colorless oil. $^1$H NMR (300 MHz, CDCl$_3$) δ8.05–8.00 (m, 2H), 7.47–7.40 (m, 3H), 5.57 (dd, J=8.8, 3.9 Hz, 1H), 4.47 (d, J=8.8 Hz, 1H), 3.67 (s, 3H), 2.45 (m, 1H), 1.01 (d, J=6.8 Hz, 6H).

d. (2S3R)-Methyl2-azo-3-dihydroxy-3-[isopropyl]propionate (XVIIIa; R$^1$=i-Pr; R$^3$=Me)

A solution of (2R,3R)-Methyl 2-bromo-3-dihydroxy-3-[isopropyl]propionate XVIIa (R$^1$=i-Pr; R$^3$=Me) (2.00 g, 6.07 mmol) in 15 mL DMSO was treated with sodium azide (790.0 mg, 12.2 mmol). After stirring for 12 h at room temperature, the mixture was partitioned between H$_2$O and ethyl acetate (50 mL each). The aqueous layer was extracted with more ethyl acetate and the combined organic layers were dried over MgSO$_4$ and concentrated in vacuo affording the desired α-azo β-benzoate (1.55 g, 87%) as a yellow oil. $^1$H NMR (300 MHz, CDCl$_3$) δ8.07–8.02 (m, 2H), 7.55–7.43 (m, 3H), 5.40 (dd, J=8.8, 2.8 Hz, 1H), 3.73 (s, 3H), 2.24 (m, 1H), 1.04 (d,J=5.8 Hz, 3H), 0.98 (d, J=5.8 Hz, 3H).

Repeating the same procedure but using DMF as the solvent instead of DMSO afforded the desired α-azo β-benzoate in 85% yield.

e. Benzamide XIXa (R$^1$=i-Pr; R$^3$=Me)

A solution of (2S,3R)-Methyl 2-azo-3-dihydroxy-3-[isopropyl]propionate XVIIIa (R$^1$=i-Pr; R$^3$=Me) (1.50 g, 5.15 mmol) in ethyl acetate (25 mL) was treated with 200 mg of 20% Pd(OH)$_2$/C and the suspension was stirred vigorously in a H$_2$ atmosphere under balloon pressure. After 12 hours, the mixture was filtered and refluxed for 4 hours to complete the migration of the benzoyl group. The mixture was then cooled to room temperature and concentrated in vacuo affording the desired benzamide (1.25 g, 92%) as a yellow oil. $^1$H NMR (300 MHz, CDCl$_3$) δ7.85–7.83 (m, 2H), 7.46–7.40 (m, 3H), 6.99 (br. d, J=9.1 Hz, 1H), 5.05 (dd, J=9.1, 1.9 Hz, 1H), 3.77 (s, 3H), 1.79 (m, 1H), 1.03 (d, J=6.7 Hz, 3H), 0.99 (d, J=6.7 Hz, 3H).

f. cis-Oxazoline Ia (R$^1$=i-Pr; R$^3$=Me)

A solution of 500 mg of benzamide XIXa (R$^1$=i-Pr; R$^3$=Me) (18.8 mmol) in CH$_2$Cl$_2$ (20 mL) was treated with 4.50 mL thionyl chloride (61.7 mmol). After stirring at room temperature for 24 h, the mixture was diluted with CH$_2$Cl$_2$ and washed with saturated NaHCO$_3$ solution, dried (Na$_2$SO$_4$), concentrated in vacuo and chromatographed (silica gel, 1:1 hexane/ethyl acetate) affording the desired cis-oxazoline (248 mg, 53%) as a pale yellow oil. $^1$H NMR(300 MHz, CDCl$_3$) δ8.01–7.97 (m, 2H), 7.52–7.38 (m, 3H), 4.94 (d, J=9.8 Hz, 1H), 4.53 (dd, J=9.8, 7.8 Hz, 1H), 3.76 (s, 3H), 2.09 (m, 1H), 1.05 (d, J=6.5 Hz, 3H), 1.01 (d, J=6.7 Hz, 3H).

EXAMPLE 11 trans-Oxazoline (Ib)

a. Ethyl 3-(isopropyl)propenoate (XV; R$^1$=i-Pr; R$^3$=Me)

To a stirred solution of carbomethoxymethylene triphenylphosphorane (56.04 g, 167.6 mmol) in dry CH$_2$Cl$_2$ (168 mL) at 0° C. was added dropwise isobutyraldehyde (17.4 mL, 191.6 mmol). After 5 min, the reaction mixture was warmed to room temperature and stirred for 24 h. The solvent was removed in vacuo and pentane was added to the white oily solid to precipitate triphenylphosphine oxide. The solid was filtered off and the filtrate concentrated in vacuo. The procedure was repeated one more time and the crude olefin (20.00 g, 93%) was obtained as a yellow oil that was sufficiently pure for the next step. $^1$H NMR (300 MHz, CDCl$_3$) δ6.95 (dd, J=15.7, 6.6 Hz, 1H), 5.77 (dd, J=15.7, 1.5 Hz), 3.72 (s, 3H), 2.44 (m, 1H), 1.06 (d, J=6.7 Hz, 6H).

b. (2R,3S)-Methyl 2,3-dihydroxy-3-[isopropyl]propionate (XVIb; $R^1$=i-Pr; $R^3$=Me)

To a clear yellow solution of $K_2OsO_2(OH)_4$ (246.1 mg, 0.67 mmol, 0.95 mol %), hydroquinine 1,4-phthalazinediyl diether (555.1 mg, 0.71 mmol, 1.01 mol %), N-methylmorpholine N-oxide (50 wt % in water, 25.0 mL, 0.106 mol, 1.51 equiv.), t-BuOH (84 mL), and $H_2O$ (58 mL) was added at 25° C. the neat olefin XV ($R^1$=i-Pr; $R^3$=Me) (9.0 g, 70.2 mmol) via a syringe pump over a period of 48 h (the syringe was connected to tubing, whose tip was immersed in the solution throughout the reaction time). The resulting clear orange solution was then stirred for another 60 min, after which time ethyl acetate (200 mL) and a solution of $Na_2SO_3$ (15.0 g) in $H_2O$ (150 mL) were added, and the resulting mixture was stirred for 4 h. The phases were separated, and the aqueous layer was extracted with more ethyl acetate (2×). The organic layers were then combined and the chiral ligand was extracted from the organic phase with a solution of 0.3 M $H_2SO_4$ in saturated $Na_2SO_4$ (2×100 mL). The phases were once again separated and the aqueous layer was extracted with more ethyl acetate (1×). The organic layers were combined and dried over $Na_2SO_4$, filtered and concentrated in vacuo. This afforded 11.4 g (ca. 100%) of a white oily solid which was shown to be 70% e.e (determined by $^1$H NMR from a 1:1 molar solution of diol and Europium tris[3-(heptafluoropropylhydroxymethylene)-(–)-camphorate] in $C_6D_6$). Recrystallisation from 35–60° C. petroleum ether afforded 6.8 g (60%) of (2R,3S)-Methyl 2,3-dihydroxy-3-[isopropyl]propionate (XVIb; $R^1$=i-Pr; $R^3$=Me) that was ca. 100% e.e., obtained as white crystals, mp=32–34° C.; =–110.6° (c 1.04, $CHCl_3$)]. $^1$H NMR (300 MHz, $CDCl_3$) δ4.28 (dd, J=5.6, 1.8 Hz, 1H), 3.80 (s, 3H), 3.48 (m, 1H), 3.28 (m, 1H), 2.33 (d, J=9.3 Hz, 1H), 1.87 (m, 1H), 1.02 (d, J=6.7 Hz, 3H), 0.95 (d, J=6.7 Hz, 3H).

c. (2S,3S)-Methyl 2-bromo-3-dihydroxy-3-(isopropyl) propionate (XVIIb; $R^1$=i-Pr; $R^3$=Me)

(2R,3S)-Methyl 2,3-dihydroxy-3-[isopropyl] propionate XVIb ($R^1$=i-Pr; $R^3$=Me) (30.0 g, 185.2 mmol) and trimethylorthobenzoate (41.3 mL, 240.7 mmol) were dissolved in $CH_2Cl_2$ (400 mL) and treated with $BF_3.OEt_2$ (1.16 mL, 9.25 mmol). After 2 h, triethylamine (1.8 mL, 13 mmol) was added, and the mixture was concentrated in vacuo and placed under full vacuum (0.05 mm Hg) for 70 min. The residue was redissolved in $CH_2Cl_2$ (400 mL), cooled to 0° C. and treated dropwise with acetyl bromide (14.3 mL, 194.5 mmol). After 2 h, additional acetyl bromide (0.68 mL, 9.25 mmol) was added. After 30 min, saturated $NaHCO_3$ solution (500 mL) was added and the mixture was stirred vigorously for 5–10 min. The layers were separated and the aqueous layer was extracted with $CH_2Cl_2$ (2×20 mL). The combined organic layers were dried ($Na_2SO_4$), filtered and concentrated in vacuo affording the crude α-bromo β-benzoate XVIIb ($R^1$=i-Pr; $R^3$=Me) (66.23 g) as a clear colorless oil, containing ~9.3% by wt. methyl benzoate. For product: $^1$H NMR (300 MHz, $CDCl_3$) δ8.05–8.00 (m, 2H), 7.47–7.40 (m, 3H), 5.57 (dd, J=8.8, 3.9 Hz, 1H), 4.47 (d, J=8.8 Hz, 1H), 3.67 (s, 3H), 2.45 (m, 1H), 1.01 (d, J=6.8 Hz, 6H).

d. (2R,3S)-Methyl 2-azo-3-dihydroxy-3-[isopropyl] propionate (XVIIIb; $R^1$=i-Pr; $R^3$=Me)

Sodium azide (24 g, 370 mmol) was added to 230 mL of DMSO and the mixture was stirred at room temperature overnight. To the resultant solution was added a solution of (2S,3S)-Methyl 2-bromo-3-dihydroxy-3-[isopropyl] propionate (XVIIb; $R^1$=i-Pr; $R^3$=Me) (61 g, 185 mmol) in 20 mL DMSO. After stirring for 11 h at room temperature, the mixture was poured into water (1.5 L) and ether (200 mL) and stirred vigorously for 10–15 min. Ether (100 mL) was added and the layers were separated. The aqueous layer was extracted with ether (2×100 mL) and the combined organic layers were washed with water (2×100 mL) and brine (100 mL), dried over $MgSO_4$, and concentrated in vacuo affording the crude product (57.5 g), containing approximately 3% starting material and 8% elimination by product. For product: $^1$H NMR (300 MHz, $CDCl_3$) δ8.07–8.02 (m, 2H), 7.55–7.43 (m, 3H), 5.40 (dd, J=8.8, 2.8 Hz, 1H), 3.73 (s, 3H), 2.24 (m, 1H), 1.04 (d, J=5.8 Hz, 3H), 0.98 (d, J=5.8 Hz, 3H).

e. Benzamide XIXb ($R^1$=i-Pr; $R^3$=Me)

To a cold (0–5° C.) solution of (2R,3S)-Methyl 2-azo-3-dihydroxy-3-[isopropyl]propionate XVIIIb ($R^1$=i-Pr; $R^3$=Me) (55 g) in methanol (300 mL) was added 94 mL of 4 M HCl/dioxane and 2.75 g of Pd(OH)$_2$/C. The mixture was purged with hydrogen and stirred at room temperature. The mixture was purged with hydrogen every 30 min to remove the liberated nitrogen. After 4 h, the reaction mixture was purged with nitrogen and additional Pd(OH)$_2$/C (1.3 g) was added. The reaction mixture was purged with hydrogen and again purged every hour for 4 h. The mixture was filtered and concentrated in vacuo. The residue was dissolved in water and extracted with EtOAc. The aqueous layer was basified with $Na_2CO_3$ and again extracted with EtOAc. The combined organic extracts were washed with brine, dried over $Na_2SO_4$, and concentrated to give a mixture of N- and O-benzoylated products, which was used directly in the next step.

f. trans-Oxazoline Ib ($R^1$=i-Pr; $R^3$=Me)

The crude product IXb obtained in Example 10e above (37.3 g, 141 mmol) was dissolved in toluene (350 mL). p-Toluenesulfonic acid (2.68 g, 14.1 mmol) was added and the mixture was heated to reflux. Water was removed using a Dean Stark trap. After 3 h, ~2.5 mL of water had been collected. The reaction mixture was cooled, diluted with EtOAc (100 mL), washed successively with saturated NaHCO; (2×100 mL) and brine (100 mL), dried over $MgSO_4$, and concentrated. The residue was purified over a pad of silica gel (400 g), eluting with 25–30% EtOAc-hexanes to provide the trans-oxazoline Ib ($R^1$=i-Pr; $R^3$=Me). $^1$H NMR (300 MHz, $CDCl_3$) δ8.01–7.97 (m, 2H), 7.52–7.38 (m, 3H), 4.68 (apparent t, J=7 Hz, 1H), 4.57 (d, J=7 Hz, 1H), 3.81 (s, 3H), 2.00–1.93 (m, 1H), 1.04 (d, J=6.7 Hz, 3H), 1.00 (d, J=6.8 Hz, 3H).

EXAMPLE 12

Inactivation of Proteasome Activity

Purification of 20S proteasome and proteasome activator PA28 was performed as previously described (Dick et al., *J. Biol. Chem.* 271:7273 (1996)).

2 mL of assay buffer (20 mM HEPES, 0.5 mM EDTA, pH 8.0) and Suc-Leu-Leu-Val-Tyr-AMC in dimethyl sulfoxide were added to a 3 mL fluorescent cuvette, and the cuvette was placed in the jacketed cell holder of a Hitachi F-2000 fluorescence spectrophotometer. The temperature was maintained at 37° C. by a circulating water bath. 0.34 mg of PA28 were added and the reaction progress was monitored by the increase in fluorescence at 440 nm ($\lambda_{ex}$=380 nm) that accompanies production of free AMC. The progress curves exhibited a lag phase lasting 1–2 min resulting from the slow formation of the 20S-PA28 complex. After reaching a steady state of substrate hydrolysis, lactacystin was added to a final concentration of 1 mM, and the reaction was monitored for 1 h. The fluorescence (F) versus time (t) data were collected on a microcomputer using LAB CALC (Galactic) software. $k_{inact}$ values were estimated by a nonlinear least-squares fit of the data to the first order equation:

$$F=A(1-e^{-kt})+C$$

where $C=F_{t=0}$ and $A=F_{t=\infty}-F_{t=0}$.

EXAMPLE 13

Inhibition of Intracellular Protein Degradation in C2C12 Cells

C2C12 cells (a mouse myoblast line) were labeled for 48 hrs with $^{35}$S-methionine. The cells were then washed and preincubated for 2 hrs in the same media supplemented with 2 mM unlabelled methionine. The media was removed and replaced with a fresh aliquot of the preincubation media containing 50% serum, and a concentration of the compound to be tested. The media was then removed and made up to 10% TCA and centrifuged. The TCA soluble radioactivity was counted. Inhibition of proteolysis was calculated as the percent decrease in TCA soluble radioactivity. From this data, an $IC_{50}$ for each compound was calculated.

EXAMPLE 14

Lactone Hydrolysis

The half-lives ($ti_{1/2}$) for hydrolysis of β-lactone analogs to the corresponding dihydroxy acids were measured at 37° C. at a concentration of 200 mM in 20 mM HEPES, 0.5 mM EDTA, pH 7.8. Absorbance was measured for at least five half-lives (approximately 1 hour) at 230 nm, the wavelength at which there is the greatest difference in extinction coefficients for the lactone and dihydroxy. Half-lives were calculated using Guggenheim analysis (Gutfreund *Enzymes: Physical Principles*; Wiley and Sons: New York, 1975, pp 118–119). The results of Examples 12–14 are reported in Table 1.

TABLE 1

Kinetics of Inhibition of 20S Proteasome and Inhibition of Intracellular Protein Degradation

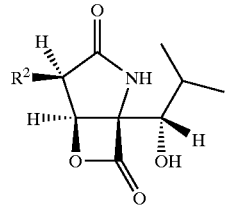

| Compound | $R^2$ | Kobs/[I] $(M^{-1}s^{-1})^a$ | $IC_{50}$ $(\mu M)^b$ | $t_{1/2}$ min$^c$ |
|---|---|---|---|---|
| 2 | Me | 20,000 | 0.7–1.1 | 13 |
| 3a | Et | 39,000 | 0.32 | 15.3 |
| 3b | n-Pr | 46,500 | 0.29 | 15.3 |
| 3c | n-Bu | 38,000 | 0.33 | 17 |
| 3d | i-Bu | 17,000 | 0.51 | 16.8 |
| 3e | CH$_2$Ph | 6,400 | — | 6.8 |
| 3f | OMe | 82,200 | 86 | 3.7 |

$^a$Inactivation of the Chymotrypsin-like activity of PA28-activated 20S proteasome.
$^b$Inhibition of intracellular protein degradation in C2C12 cells.
$^c$Hydrolysis half-life The results indicate that the compounds of the present invention are potent inhibitors of the proteasome.

EXAMPLE 15

Reduction of Infarct Size and Neuronal Loss

Methods

Male Sprague Dawley rats (250–400 g) were anesthetized with haloethane and subjected to middle cerebral artery (MCA) occlusion using a nylon filament for 2 h. Subsequently, the filament was removed and reperfusion of the infarcted tissue occurred for 24 hours before the rat was sacrificed.

Immediately after the filament was withdrawn, the animals were evaluated using a neurological scoring system. Neurological scores were expressed on a scale from 0 to 10, with 0 representing no neurological deficit and 10 representing severe neurological deficit. After 24 hours and before sacrifice, animals were evaluated a second time using the same neurological scoring system.

Staining of coronal sections (2.0 mm×7–8) with triphenyltetrazolium chloride (TTC) taken throughout the brain were evaluated under blinded conditions using image analysis to determine infarct size.

Dosing Regimen

Rats were given i.v. bolus injections (1.0 mL/kg) of either vehicle (50% propylene glycol/saline; n=8) or 7-n-propyl-clasto-lactacystin β-lactone (3b) (0.3 mg/kg; n=7) at 2 hours after the start of the occlusion. Two additional groups of rats were given i.v. bolus injections (1.0 mL/kg) of 3b at 0 minutes, 2 hours, and 6 hours after the start of the occlusion. One group (0.1 mg/kg×3; n=6) received 0.1 mg/kg at each of these times, while another group (0.3 mg/kg×3; n=7) received 0.3 mg/kg at each of the three timepoints.

Results

In animals treated with a single dose of 7-n-propyl-clasto-lactacystin β-lactone (3b), infarct volume was decreased by 50% (FIG. 1, 0.3×1). Infarct volume was not significantly decreased in either the 0.1 mg/kg×3 dosage group or the 0.3 mg/kg×3 dosage group (FIG. 1).

All animals had a neurological score of 10±0 immediately after the 2 hour ischemic episode. At 24 hours, the vehicle-treated rats had a mean score of 8.7±0.6, whereas rats treated with a single 0.3 mg/kg dose of 7-n-propyl-clasto-lactacystin β-lactone (3b) had a mean score of 4±1 (FIG. 2) These data represent a 60% neurological improvement for the drug-treated animals. No significant improvement in neurological score was observed in either the 0.1 mg/kg×3 dosage group of the 0.3 mg/kg×3 dosage group (FIG. 2).

Conclusion 7-n-propyl-clasto-lactacystin β-lactone, given once post-ischemia, provides significant protection in both the degree of neurological deficit and infarcted brain damage. From these preliminary data, it appears that a single-dose regimen is preferred over a multiple-dose regimen.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A process for forming a substituted aryl oxazoline compound of Formula Ia:

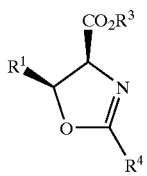

wherein
- $R^1$ is alkyl, alkenyl, alkynyl, cycloalkyl, aryl, alkaryl, aralkyl, where the ring portion of said aryl, aralkyl, or alkazyl can be optionally substituted;
- $R^3$ is alkyl, cycloalkyl, aryl, alkaryl, any of which can be optionally substituted; and
- $R^4$ is optionally substituted aryl or optionally substituted heteroazyl; said method comprising:

(a) asymmetrically dihydroxylating an alkene intermediate of Formula XV:

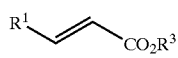

to form an optically active diol of Formula XVIa:

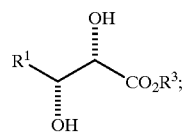

(b) reacting said optically active diol of Formula XVIa with an orthoester under acid catalysis to give a mixed orthoester, and thereafter reacting the resulting mixed orthoester intermediate with a reagent selected from the group consisting of acyl halides, HCl, HBr, HI, Me$_3$SiCl, Me$_3$SiI, Me$_3$SiBr and halogen-containing Lewis acids to form a haloester derivative of Formula XVIIa:

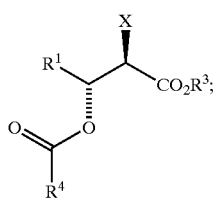

wherein X is Cl Br, or I;

(c) reacting said haloester derivative with an alkali metal azide to form an azide of Formula XVIIIa:

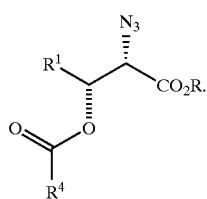

2. The process of claim 1, wherein in step (a) the dihydroxylation reaction is conducted with AD-mix-β in the presence of methane sulfonamide to stereoselectively afford the diol of Formula XVIa.

3. The process of claim 1, wherein in step (a) the dihydroxylation reaction is conducted using an N-oxide as a reoxidant.

4. The process of claim 1, wherein in step (b) said diol of Formula XVIa is treated with an orthoester under Lewis or Brönsted acid catalysis to give a mixed orthoester, which is converted in situ to a haloester of Formula XVIIa wherein X is Br by treatment with acetyl bromide.

5. The process of claim 4, wherein the orthoester employed in this reaction is an aromatic carboxylic acid orthoester.

6. The process of claim 5, wherein the orthoester is trimethyl orthobenzoate.

7. The process of claim 4, wherein said acid catalyst is HBr, SnCl$_4$, TiCl$_4$, BBr$_3$, or boron trifluoride.

8. The process of claim 1, wherein in step (c) crude haloester of Formula XVIIa is converted to the azide of Formula XVIIIa by treatment with an alkali metal azide in a polar aprotic organic solvent.

9. The process of claim 1, wherein in step (d) said catalytic hydrogenation of the azide of Formula XVIIIa is conducted over a palladium catalyst in ethyl acetate.

10. The process of claim 9, wherein said catalytic hydrogenation proceeds with concomitant migration of the aroyl group to afford the hydroxyamide of Formula XIXa.

11. The process of claim 1, wherein in step (e) the hydroxyamide of Formula XIXa is treated with thionyl chloride in methylene chloride to effect ring closure with inversion of the hydroxyl to produce the cis-substituted oxazoline of Formula Ia.

12. The process of claim 11, wherein the cis-oxazoline is converted to the trans-oxazoline under equilibrating condition by inversion of configuration of the ester substituents.

13. A process for forming a substituted aryl oxazoline compound of Formula Ib:

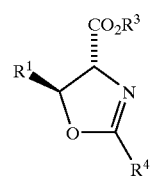

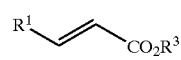

to form an optically active diol of Formula XVIb:

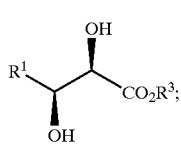

(b) reacting said optically active diol of Formula XVIb with an orthoester under acid catalysis to give a mixed orthoester, and thereafter reacting the resulting mixed orthoester intermediate with a reagent selected from the group consisting of acyl halides, HCl, HBr, HI, Me$_3$SiCl, Me$_3$SiI, Me$_3$SiBr and halogen-containing Lewis acids to form a haloester derivative of Formula XVIIb:

XVIIb

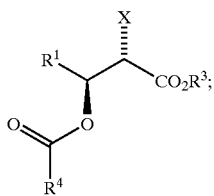

wherein X is Cl, Br, or I;

(c) reacting said haloester derivative with an alkali metal azide to form an azide of Formula XVIIIb:

XVIIIb

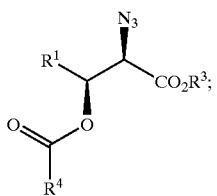

(d) hydrogenating said azide to form a compound of Formula XIXb:

XIXb

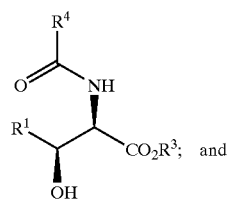

(e) subjecting the compound of Formula XIXb to ring closing conditions to form said substituted phenyloxazoline of Formula Ib; wherein for each of Formulae XVb, XVIb, XVIIb, XVIIIb and XIXb, $R^1$, $R^3$ and $R^4$ are as defined above for Formula Ib.

14. The process of claim 13, wherein in step (a) the dihydroxylation reaction is conducted with AD-mix-α in the presence of methane sulfonamide to stereoselectively afford the diol of Formula XVIb.

15. The process of claim 13, wherein in step (a) the dihydroxylation reaction is conducted using an N-oxide as a reoxidant.

16. The process of claim 13, wherein in step (b) said diol of Formula XVIb is treated with an orthoester under Lewis or Brönsted acid catalysis to give a mixed orthoester, which is converted in situ to a haloester of Formula XVIIb wherein X is Br by treatment with acetyl bromide.

17. The process of claim 16, wherein the orthoester employed in this reaction is an aromatic carboxylic acid orthoester.

18. The process of claim 17, wherein the orthoester is trimethyl orthobenzoate.

19. The process of claim 16, wherein said acid catalyst is HBr, $SnCl_4$, $TiCl_4$, $BBr_3$ or boron trifluoride.

20. The process of claim 13, wherein in step (c) crude haloester of Formula XVIIb is converted to the azide of Formula XVIIIb by treatment with an alkali metal azide in a polar aprotic organic solvent.

21. The process of claim 13, wherein in step (d) said catalytic hydrogenation of the azide of Formula XVIIIb is conducted over a palladium catalyst in ethyl acetate.

22. The process of claim 21, wherein said catalytic hydrogenation proceeds with concomitant migration of the aroyl group to afford the hydroxyamide of Formula XIXb.

23. The process of claim 13, wherein in step (e) the hydroxyamide of Formula XIXb is treated with thionyl chloride in methylene chloride to effect ring closure with inversion of the hydroxyl to produce the trans-substituted oxazoline of Formula Ib.

\* \* \* \* \*

UNITED STATES PATENT AND TRADEMARK OFFICE
CERTIFICATE OF CORRECTION

PATENT NO. : 6,794,516 B2
DATED : September 21, 2004
INVENTOR(S) : Francois Soucy et al.

It is certified that error appears in the above-identified patent and that said Letters Patent is hereby corrected as shown below:

<u>Column 43,</u>
Line 15, please change "alkazyl" to -- alkaryl --.
Line 19, please change "heteroazyl;" to -- heteroaryl; --.
Line 60, please add the following paragraphs formula XVIIIa:

(d)  hydrogenating said azide to form a compound of Formula *XIXa*:

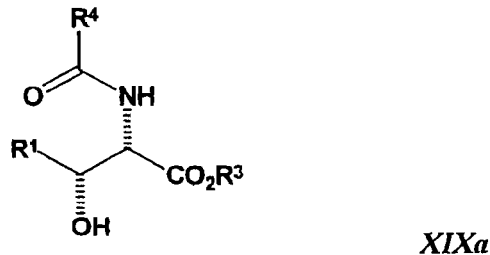

*XIXa* and (e)  subjecting the compound of Formula *XIXa* to ring closing conditions to form said substituted phenyloxazoline of Formula *Ia*;

wherein for each of Formulae *XVa, XVIa, XVIIa, XVIIIa* and *XIXa*, $R^1$, $R^3$ and $R^4$ are as defined above for Formula *Ia*.

UNITED STATES PATENT AND TRADEMARK OFFICE
CERTIFICATE OF CORRECTION

PATENT NO. : 6,794,516 B2
DATED : September 21, 2004
INVENTOR(S) : Francois Soucy et al.

It is certified that error appears in the above-identified patent and that said Letters Patent is hereby corrected as shown below:

Column 44,
Line 40, please add the following paragraphs forluma Ib:

wherein
$R^1$ is alkyl, alkenyl, alkynyl, cycloalkyl, aryl, alkaryl, aralkyl, where the ring portion of said aryl, aralkyl, or alkaryl can be optionally substituted;
$R^3$ is alkyl, cycloalkyl, aryl, alkaryl, any of which can be optionally substituted; and
$R^4$ is optionally substituted aryl or optionally substituted heteroaryl;
said method comprising:
(a) asymmetrically dihydroxylating an alkene intermediate of Formula XV:

Signed and Sealed this

Twenty-second Day of November, 2005

JON W. DUDAS
*Director of the United States Patent and Trademark Office*